(12) United States Patent
Sjöstedt et al.

(10) Patent No.: US 11,152,097 B2
(45) Date of Patent: Oct. 19, 2021

(54) MEDICAL DEVICE WITH SAFETY FEATURES

(71) Applicant: BRIGHTER AB (PUBL), Kista (SE)

(72) Inventors: Truls Sjöstedt, Täby (SE); Leif Hall, Bromma (SE)

(73) Assignee: BRIGHTER AB, Stockholm (SE)

( * ) Notice: Subject to any disclaimer, the term of this patent is extended or adjusted under 35 U.S.C. 154(b) by 0 days.

(21) Appl. No.: 16/595,881

(22) Filed: Oct. 8, 2019

(65) Prior Publication Data

US 2020/0061300 A1 Feb. 27, 2020

Related U.S. Application Data

(63) Continuation of application No. 15/037,128, filed as application No. PCT/SE2014/051392 on Nov. 20, 2014, now Pat. No. 10,596,324.

(30) Foreign Application Priority Data

Nov. 20, 2013 (SE) .................................. 1351376-7

(51) Int. Cl.
*G16H 20/17* (2018.01)
*A61M 5/31* (2006.01)
(Continued)

(52) U.S. Cl.
CPC ......... *G16H 20/17* (2018.01); *A61B 5/14532* (2013.01); *A61B 5/151* (2013.01);
(Continued)

(58) Field of Classification Search
None
See application file for complete search history.

(56) References Cited

U.S. PATENT DOCUMENTS 4,413,991 A * 11/1983 Schmitz .............. A61M 5/2066
604/191
5,279,586 A 1/1994 Balkwill
(Continued)

FOREIGN PATENT DOCUMENTS

DE 102010015094 A1 10/2011
EP 0777123 A3 5/2002
(Continued)

OTHER PUBLICATIONS

International Preliminary Report on Patentability from corresponding International Patent Application No. PCT/SE2014/051392, mailed by the ISA dated May 24, 2016.
(Continued)

*Primary Examiner* — Jenna Zhang
(74) *Attorney, Agent, or Firm* — Tucker Ellis LLP

(57) ABSTRACT

A portable medical device for injecting a medicament into a patient. The device includes a control circuit with a memory, the control circuit automatically storing in the memory an ejection event including an amount of the medicament that is ejected from the portable medical device during the ejection event; and a proximity sensor configured to sense proximity of a solid object located in an ejection direction of the portable medical device without making contact with the solid object. The control circuit is configured to tag the ejection event as an injection event if the ejection takes place in proximity of the solid object and to tag the ejection event as a priming ejection if the ejection does not take place in proximity of the solid object.

12 Claims, 15 Drawing Sheets

(51) Int. Cl.
*A61M 5/315* (2006.01)
*A61M 5/24* (2006.01)
*A61B 5/151* (2006.01)
*A61B 5/15* (2006.01)
*G06F 19/00* (2018.01)
*G16H 40/63* (2018.01)
*A61B 5/145* (2006.01)
*A61B 5/157* (2006.01)

(52) U.S. Cl.
CPC ........ *A61B 5/157* (2013.01); *A61B 5/150022* (2013.01); *A61B 5/15117* (2013.01); *A61B 5/15125* (2013.01); *A61B 5/150954* (2013.01); *A61M 5/24* (2013.01); *A61M 5/3146* (2013.01); *A61M 5/31533* (2013.01); *A61M 5/31551* (2013.01); *A61M 5/31585* (2013.01); *G06F 19/00* (2013.01); *G16H 40/63* (2018.01); *A61B 5/150358* (2013.01); *A61B 2562/0295* (2013.01); *A61M 5/31593* (2013.01); *A61M 2005/3126* (2013.01); *A61M 2205/13* (2013.01); *A61M 2205/3306* (2013.01); *A61M 2205/3553* (2013.01); *A61M 2205/50* (2013.01); *A61M 2205/502* (2013.01); *A61M 2205/52* (2013.01); *A61M 2205/58* (2013.01); *A61M 2205/8212* (2013.01); *A61M 2230/201* (2013.01)

(56) References Cited

U.S. PATENT DOCUMENTS

| | | | |
|---|---|---|---|
| 5,536,249 A * | 7/1996 | Castellano | G16H 20/17 604/65 |
| 5,593,390 A | 1/1997 | Castellano | |
| 5,925,021 A | 7/1999 | Castellano | |
| 6,192,891 B1 | 2/2001 | Gravel | |
| 6,221,046 B1 | 4/2001 | Burroughs | |
| 8,350,216 B2 | 1/2013 | Yao | |
| 8,536,507 B2 | 9/2013 | Fadell | |
| 2004/0210199 A1 | 10/2004 | Atterbury | |
| 2008/0009811 A1 * | 1/2008 | Cantor | A61B 17/205 604/272 |
| 2009/0216182 A1 * | 8/2009 | Lauchard | A61M 5/20 604/65 |
| 2010/0207879 A1 * | 8/2010 | Fadell | G06F 3/04883 345/156 |
| 2011/0270214 A1 * | 11/2011 | Jorgensen | A61M 5/31551 604/500 |
| 2011/0282173 A1 * | 11/2011 | Fonduca | A61B 5/150748 600/365 |
| 2011/0313350 A1 * | 12/2011 | Krulevitch | A61M 5/31525 604/65 |
| 2012/0046606 A1 | 2/2012 | Arefieg | |
| 2014/0380218 A1 | 12/2014 | Johnnie | |

FOREIGN PATENT DOCUMENTS

| | | |
|---|---|---|
| EP | 1048310 A3 | 11/2002 |
| EP | 1688085 A1 | 8/2006 |
| GB | 2491984 A | 12/2012 |
| JP | 2007 313374 A | 12/2007 |
| WO | 02066101 A2 | 8/2002 |
| WO | 2009027950 A2 | 3/2009 |
| WO | 2009083600 A1 | 7/2009 |
| WO | 2010091005 A1 | 8/2010 |
| WO | 2010/098927 A1 | 9/2010 |
| WO | 2012068214 A1 | 5/2012 |
| WO | 2012/107493 A1 | 8/2012 |
| WO | 2013024160 A2 | 2/2013 |
| WO | 2013053695 A1 | 4/2013 |
| WO | 2013024160 A3 | 6/2013 |

OTHER PUBLICATIONS

Extended European Search Report from corresponding European Patent Application No. 17198256.4, dated Feb. 16, 2018.
International Search Report from corresponding International Patent Application No. PCT/SE2014/051392, mailed by the ISA dated Feb. 20, 2015.
Extended European Search Report from corresponding European Patent Application No. 14864054.3, dated Oct. 25, 2016, 9 pages.

* cited by examiner

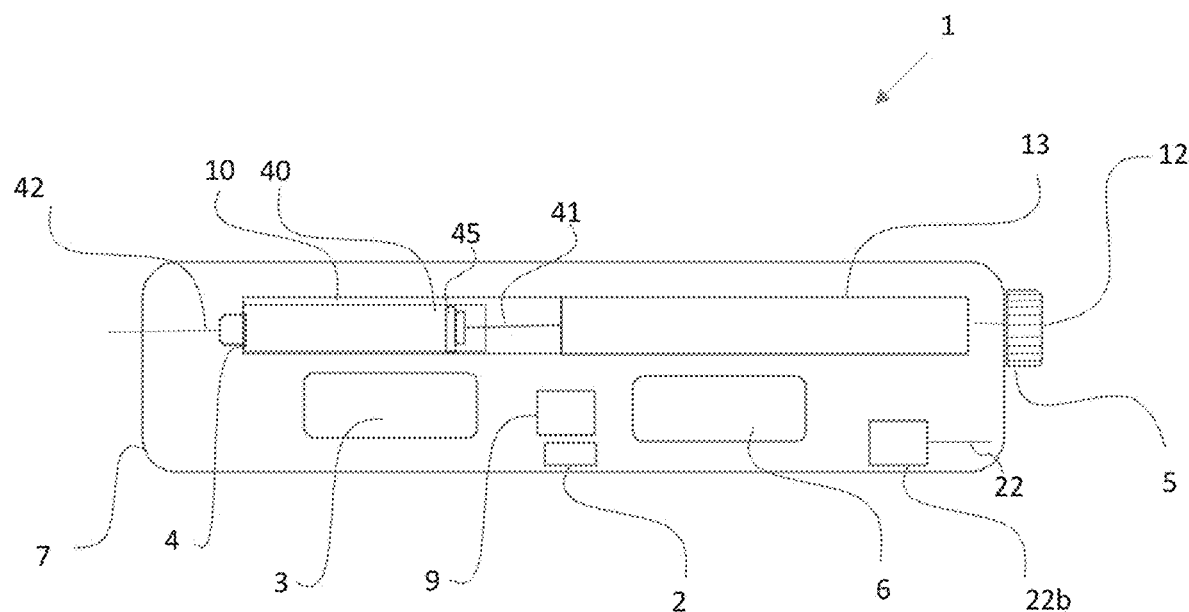
FIG 1
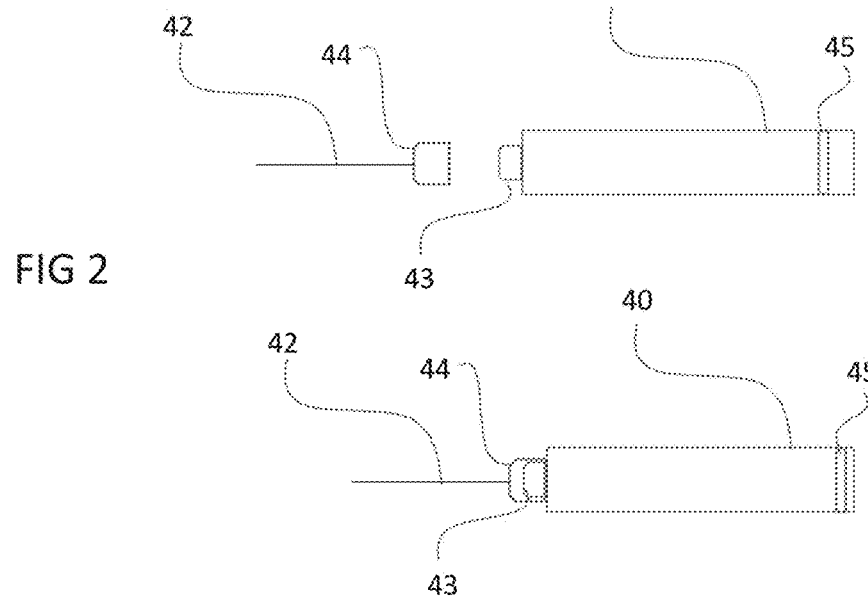
FIG 2
FIG 3

MEDICAL DEVICE WITH SAFETY FEATURES

RELATED APPLICATION DATA

This application is a continuation of U.S. patent application Ser. No. 15/037,128, filed May 17, 2016, which is a U.S. National Phase of International Patent Application No. PCT/SE2014/051392, filed Nov. 20, 2014, which claims the benefit of Swedish Patent Application No. 1351376-7, filed Nov. 20, 2013, the disclosures of these applications are incorporated herein by reference in their entireties.

The present invention relates to an improved device for injecting a medicament to be used by diabetes patients, or other patients that self-medicate injectable drugs.

BACKGROUND OF THE INVENTION

Diabetes patients that inject insulin have to check their blood glucose value and carry out insulin injections, sometimes several times every day. They also need to log their blood glucose values and register the amount of insulin that has been injected in order to monitor the disease. Today this requires several different devices: means for testing blood glucose including means for taking a blood sample (such as a lancet), disposable test strips and a blood glucose meter; an insulin injection device, extra insulin cartridges, replacement needles and also a log book and writing utensils for registering blood glucose values and injections. The diabetic patient has to carry all these items with him or her, which is not only a hassle but also a risk for the patient, since losing equipment puts him or her at danger, since proper treatment is then perhaps not achieved.

The amount of insulin that the patients injects is based on the blood glucose measurements. Injection of an incorrect amount of insulin is dangerous to the patient. Therefore it is important that this procedure is carried out in a correct and safe manner.

Furthermore, since it is very important that the patient actually treats him or herself it is desirable that self-medication causes minimal inconvenience for the patient and affect the patient's life style as little as possible.

In order to solve this problem there has been developed devices that integrates all these functionalities, for example WO2009027950 which describes a portable medical device that integrates blood glucose measurement and insulin injection. It has a lancet for obtaining a blood sample. The lancet, and the injections means are placed on the same end of an elongated housing in order to avoid blood splashing getting in touch with mechanical movable parts and/or electronic parts inside the housing.

The site http://www.brightercompany.com/product-information as visited on Nov. 6, 2013 has a film that discloses a medical device. It has a test strip port located adjacent and such that the test strip is parallel to the injection needle. It has one display that shows both blood glucose concentration and the amount of insulin to be injected by the device.

The diabetes patient is used to carry out the different steps of blood glucose measurement and insulin injection in a certain order and in a certain manner. This contributes to that the patient carries out the procedure in a safe manner. This is particularly important since the cognitive abilities of diabetes patients may sometimes be compromised due to fluctuating blood glucose levels.

There is also a need for improved logging of injections. Currently registration of blood glucose measurement are usually carried out manually by the patient. Manual registrations are prone to human errors, for example the patient may forget to register a value or enters the wrong value. Automatic logs have been proposed, for example in WO2012068214.

Before each injection it is important that the user primes the injection needle, in order to ensure that there are no air bubbles and no clogs in the needle. This is carried out by ejecting a small amount of medication from the needle. A disadvantage with current automatic logs is that they cannot distinguish between injection events and priming events. WO 2009083600 proposes a medical device that can log insulin injections and distinguish between injections events and priming events depending on the speed of the ejected liquid during ejection. However, that invention assumes that the ejection speed is controlled by the device. In devices where the injection speed varies, for example because the user pushes a plunger with different speed from time to time, such a solution cannot be used.

Thus, there is a need for improved log that can distinguish between injection events and priming events in safe and convenient manner.

SUMMARY OF THE INVENTION

In a first aspect of the invention there is provided a portable medical device for injecting insulin comprising a) blood glucose meter, b) a first display that is capable of displaying the glucose concentration of a blood sample as determined by the blood glucose meter, and c) means for injecting insulin in a patient comprising means for setting the amount of insulin to be ejected by the device, comprising a second display that shows the amount of insulin to be ejected, where the device comprises a deactivation means that switches off the first display when the means for setting the amount of insulin to be ejected is set to a setting that permits the ejection of insulin.

The device has the advantage that the user does not confuse the blood glucose measurement shown on the first display with the setting of the insulin injection means. The user does not think that the value of the blood glucose measurement is the amount of insulin that he or she has just injected. Thus, the user is guided through the procedure in a step by step fashion.

The first display can be an electronic display such as an LCD or an OLED display. This has the advantage that the display is small and can show a multitude of symbols and figures, and moving objects.

The second display can be a mechanical display. Mechanical displays are very reliable and does not require the use of electricity. This has the advantage that the entire injection means can be user-powered, which results in reliable and battery-free operation. The fact that there are no electrical components results in the injection means also decreases the risk for electric shock for the user.

The deactivation means may comprise a sensor that senses when the means for setting the amount of insulin to be ejected is set to a setting that permits the ejection of insulin. The sensor may be a position sensor.

The sensor is suitably connected to a processing unit that controls the first display. The deactivation means may also include a processing unit and connections between sensor, processing unit and the first display.

The drive mechanism of the means for injecting insulin is preferably powered by the user.

In one embodiment, the first display is automatically switched on when the means for setting the amount of insulin to be ejected is set to a setting that does not permit the ejection of insulin.

The work flow when using the device is preferably indicated on the device so that the user makes a mental connection between each of the various steps to different ways of interacting with the device. This can achieved as follows.

The housing of the device can be arranged to further separate the various components. For example, the angle between a line that is perpendicular to the surface of the first display and a line that is perpendicular the surface of the second display may be at least 60°.

When the device is a multifunctional device that also includes a lancet for making a blood sample, the device can be further designed to further separate the different steps of taking a blood sample, making a blood glucose measurement and injecting insulin. Assigning the various functions to ways of interacting with the device the user is guided along the procedure. The ways of interacting with the device is distinct for each of the steps of taking a blood sample, making a blood glucose measurement, injecting insulin and logging events. The design of the inventive device makes it easier to remember the correct sequence of the various procedures.

Thus the device may have a housing and the device additionally comprises a site for connecting a lancet located in one end of the housing and where the means for injecting insulin includes a cartridge housing for receiving an insulin cartridge where said insulin cartridge can be connected to an injection needle, said injection needle being located, when connected to the cartridge, in the opposite end of the housing and where an injection actuator is located in the same end of the housing as the site for connecting a lancet.

The first display may be located on the housing approximately in the middle between the site for connecting a lancet and the site for connecting the injection needle on the insulin cartridge. The angle between the lancet and the injection needle may be from about 160° to −220°.

When the device has a site for connecting a lancet and where the blood glucose meter comprises a test strip port such that the angle between the test strip, when inserted into the test strip port, and the lancet may be from 45° to 135°. The angle between the test strip, when inserted into the test strip port, and the injection needle, when attached, may be from 45° to 135°, In a second aspect of the invention it is provided a method for logging insulin injections carried out by a medical device with injection means comprising the steps of a) determining the amount of insulin that was ejected by the medical device, b) storing, in the memory of the device, the time of ejection together with data from a) as an ejection event, c) determining, with a proximity sensor in the device, said proximity sensor able to sense the proximity of a solid object in the direction of the injection needle, if ejection by the medical device takes place in the proximity of a solid object, and d) tagging the ejection event as an injection event if the ejection takes place in the proximity of a solid object and tagging the ejection event as a priming event if the ejection does not take place in the proximity of a solid object.

The method can be used for logging events in electronic log that can be conveniently accessed by the user through a user interface on the device. The electronic log is an improvement of current logs that cannot distinguish between real injections and priming ejections. Thus the user is provided with a reliable log for injections and glucose measurements which improves safety.

Preferably an ejection event is tagged as an injection event if, when insulin is ejected by the device, there is a solid object within a threshold distance of the medical device. The threshold distance may be 200 mm.

In an alternative embodiment where an ejection event is tagged as an injection event if, when insulin is ejected, the distance from the sensor to the tip of the needle ($D_1$) is larger than the distance from the sensor to a solid object ($D_2$) and where $D_1$-$D_2$≥0.1 mm. In one embodiment the method is such that information about the injection events are accessible to the user thought a user interface on the medical device and information about the priming events are not accessible to the user via a user interface on the medical device. The priming events are only accessible, for example through a data port, or after entering a code. Thus, the priming events are not visible to the user. This has the advantage that the user does not confuse the priming events with real injections in the log. However, the priming events are still accessible for doctors and nurses and persons that carry out service on the device.

In one embodiment the method comprises the additional step of the user using a user interface to tag an injection event with additional information regarding one selected from the group consisting of a blood glucose measurement, health status, taking a meal and exercise.

In one embodiment the method comprises the additional step of the device automatically tagging an injection event with a blood glucose measurement if the blood glucose measurement has been made within 30 min of the time point of the injection event. Blood glucose measurements are affected by insulin injections, meals, exercise and illness. The advantage of this arrangement is that, when the user reviews blood glucose measurements, he or she can take meals, etc. into account in a convenient manner. The advantage with automatic tagging is that tagging occurs even if the user forgets to tag.

In a third aspect of the invention there is provided a medical device suitable to carry out the method of the invention. Thus there is provided portable medical device for injecting insulin comprising a means for injecting insulin in a patient, means for automatically recording the amount of insulin that is injected at a certain time point as an injection event and a proximity sensor that can sense the proximity of a solid object in the same direction as the injection needle where the medical device is configured to tag the ejection event as an injection event if the injection takes place in the proximity of a solid object and tagging the ejection event as a priming ejection if the ejection does not take place in the vicinity of an object. The sensor is suitable an infrared sensor. The device can be configured to tag ejections as injections when the distance from the front plate of the cartridge housing to an object is less than a threshold value T that is described in more detail below. The threshold value can be 200 mm.

Definitions

As used herein, "user" and "patient" refers to the person that uses the device to test blood glucose and inject himself or herself with insulin.

Although it is frequently referred to insulin in this application, the inventions disclosed herein may be useful for devices for injecting other medicaments that are self-administered by the patient, such as, for example growth hormone.

"Insulin" covers not only insulin in its natural form but also insulin variants and analogs that are administered to diabetic patients.

"Tagging" means storing additional information about a database entry in a database.

"Ejection" means expulsion of a liquid medicament from a medical device with injection means, for example by a plunger creating a pressure. Typically ejection is carried out from the tip of an injection needle which can be attached to the device.

"Injection" is ejection where the liquid medicament, after being ejected, enters into a solid object (typically the body of a patient).

"Priming" is ejection where ejection does not take place into a solid object. For example the liquid medicament may be sprayed into the air, or drip from the tip of the needle.

When it is referred to "date and time" or similar herein, it is meant a fixed time point. A fixed time point does not necessarily have to be expressed as date and time.

BRIEF DESCRIPTION OF DRAWINGS

FIG. 1 is a schematic overview of the interior of a medical device.

FIGS. 2-3 are schematic overviews of an injection needle and an insulin cartridge.

FIG. 7 shows the interior of a medical device and FIGS. 8-9 shows the exterior.

DESCRIPTION OF EXEMPLARY EMBODIMENTS

Figure 4:
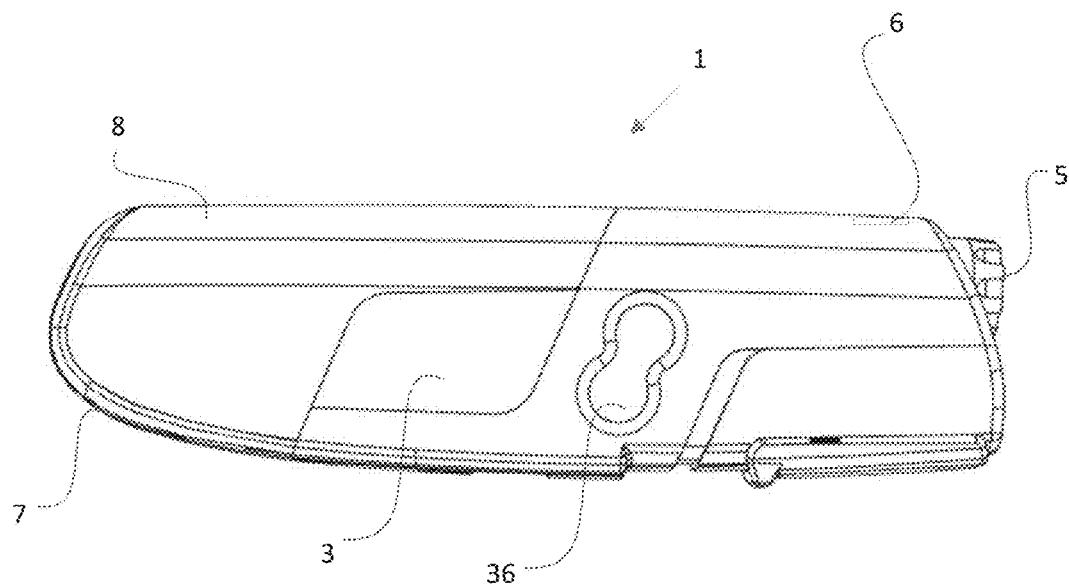
FIGS. 4-5 shows examples of the exterior of the device.

FIG. 1 is a general schematic overview of the medical device 1, which in a preferred embodiment comprises injection means comprising a cartridge housing 10. The cartridge 40 is placed by the user in the cartridge housing 10 of the device 1. Injection of insulin is carried out with a needle 42 the needle hub 44 of which is attached to the top 43 of cartridge 40 by the user as shown in FIGS. 2 and 3. The cartridge 40 and the needle 42 are usually supplied separately from the device 1 and does not form a part of this invention. Returning to FIG. 1, the injection means further comprises a drive mechanism 13 that causes the ejection of insulin through the needle 42 and means for setting the amount of insulin to be injected 5 (dose setting means).

Figure 14:
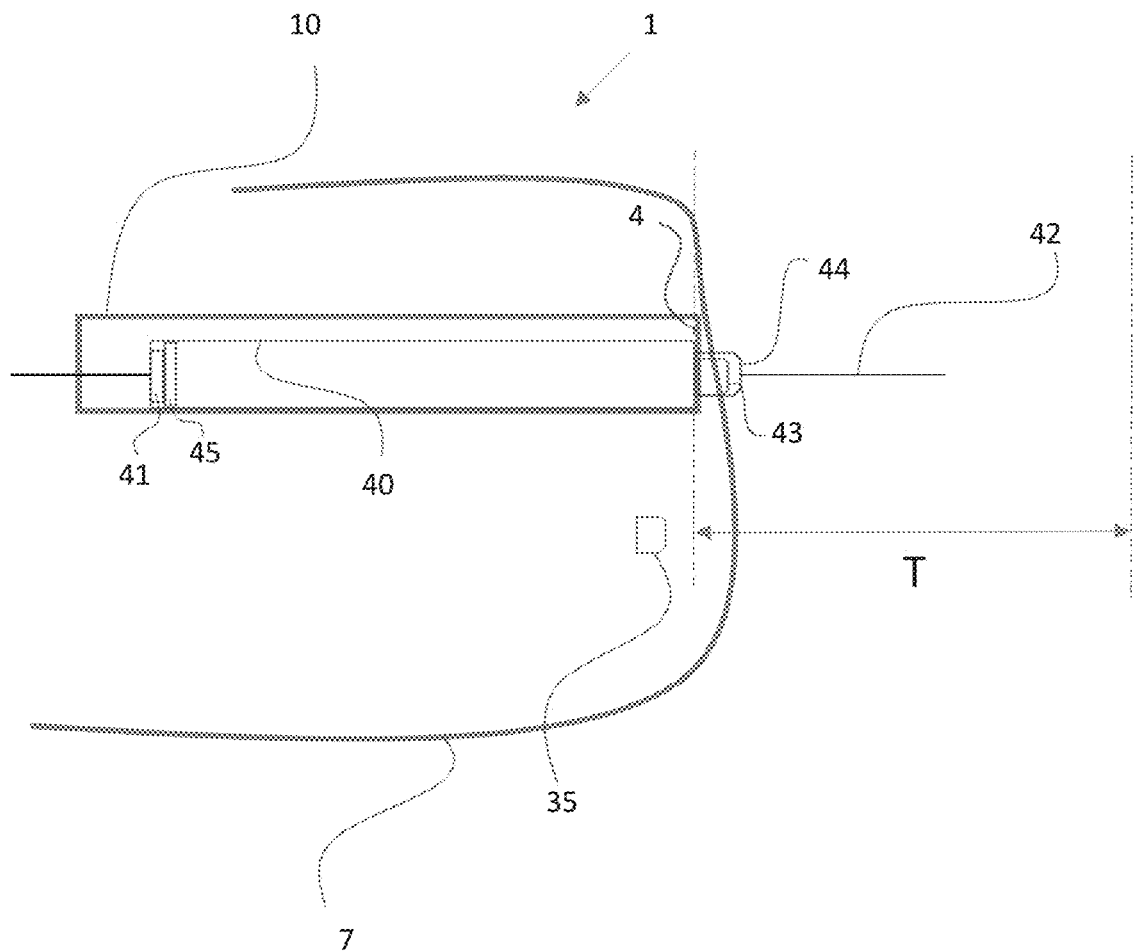
FIG. 14 shows the threshold distance for a proximity sensor in the device.

The drive mechanism 13 can comprise a plunger 41 that causes the ejection of medicament through the needle 42 when it travels in the longitudinal direction of the cartridge housing. The plunger 41 may be adapted push on a second plunger 45 supplied in the cartridge 40. The front of the main part of the cartridge 40 can rest against the front plate 4 of the cartridge housing 10 as shown in FIG. 14 (note that the needle points in the opposite directions in FIG. 1 and FIG. 14).

Suitably the device 1 also comprises a blood glucose meter 9.

Preferably the device 1 is portable. Then the user can easily bring the device with him or her.

A preferred design of the device 1 comprises a housing 7 which is a hollow body that contains the various parts of the device 1. Preferably the housing 7 is of a size and shape that enables the user to rest the device in the hand. The housing may have one or more detachable parts that serves as cover 8, for example as cover for the injection needle. The housing can be made of plastic or metal, where plastic is a preferred material. The drive mechanism 13 is preferably enclosed in the housing 7, as is processing unit 19 and glucose meter 9.

Typically the device 1 is used in the following manner. First the user uses the lancet 22 to puncture the skin in order to obtain a drop of blood. The drop is then brought in contact with the end of a test strip. The other end of the test strip is entered into blood glucose meter 9 through the test strip port 2. The blood glucose meter 9 then carries out measurement of the glucose content of the blood and presents a blood glucose concretion value to the user on a display 3. Based on this value, the user decides how much insulin that is to be injected. The user then sets the amount of insulin with the dose setting means 5 and injects himself/herself.

The device 1 has a user interface with at least one display. The display can show various kinds of information, such as blood glucose measurements, injection events, date and time. The device 1 has injection means, including a display that shows the amount of insulin to be injected and a drive mechanism 13 that preferably is powered by the user (user-powered). Such injection means has proven to be very reliable, as they require no electricity and the drive mechanisms can be made very durable. Examples of user-powered drive mechanism for injecting insulin includes mechanisms that are powered by the user pressing an injection actuator. The pressing power is mechanically transferred to the plunger 41. Examples of user-powered drive mechanism are known in the art, examples include U.S. Pat. Nos. 5,593,390, 6,221,046, 5,279,586 and WO2009027950. A user-powered drive mechanism may suitably have a mechanical display. These require no electricity and are very reliable.

However, it is also desirable that the device 1 has a display that is small, light and that can show a variety of symbols and letters and that can be easily connected to a microprocessor. Therefore, in a preferred embodiment, the device 1 has two displays; a first display 3 which is non-mechanical, preferably an electronic display such as an OLED, a PDP or an LCD display, and a second display 6 which is mechanical and which shows the dose setting.

FIG. 4 shows an example of the exterior of the device 1. In the housing 7 is mounted first display 3. The second display 6 and dose setting means 5 are also visible. A part of the housing 7 forms a removable cap 8 that protects the injection needle. Thus when the cap 8 is on, the needle 42 is inside the housing 7.

Figure 5:
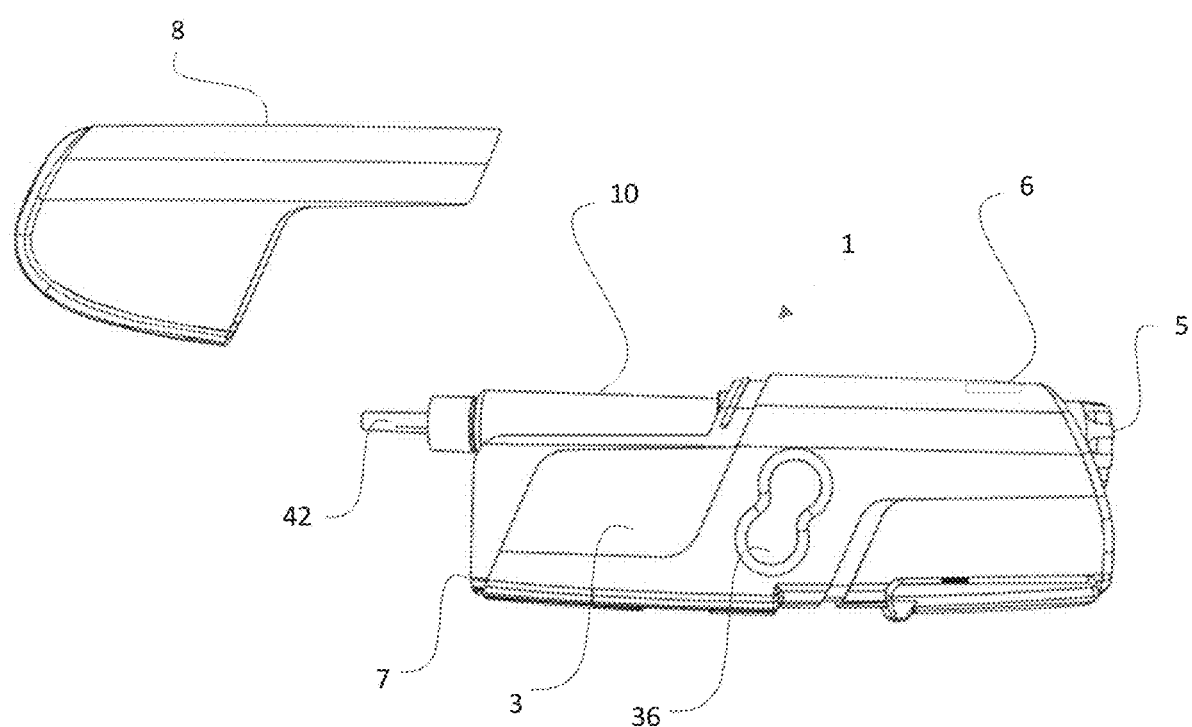

FIG. 5 shows essentially the same as FIG. 5, as it shows the housing 7 of the device 1 with the cap 8 removed to expose the cartridge housing 10, needle 42 (with an additional protective cap). First display 3, second display 6 and dose setting means 5 are also visible.

The medical device 1 will now be described in more detail with reference to FIG. 1. Preferably the device 1 is equipped with a blood glucose meter 9 as shown in FIG. 1. Blood glucose meters are well known in the art. Usually blood glucose measurement is carried out with disposable test strips 28 as is well known in the art. The test strip 28 may be of the kind that contains one or more chemicals that react with glucose in the blood in such a way that the blood glucose concentration can be measured. For example the test strip is a standard glucose oxidase/ferrocyanide test strip where the glucose concentration affects an electric current in a way that can be converted to a blood glucose concentration measurement.

Figure 13:
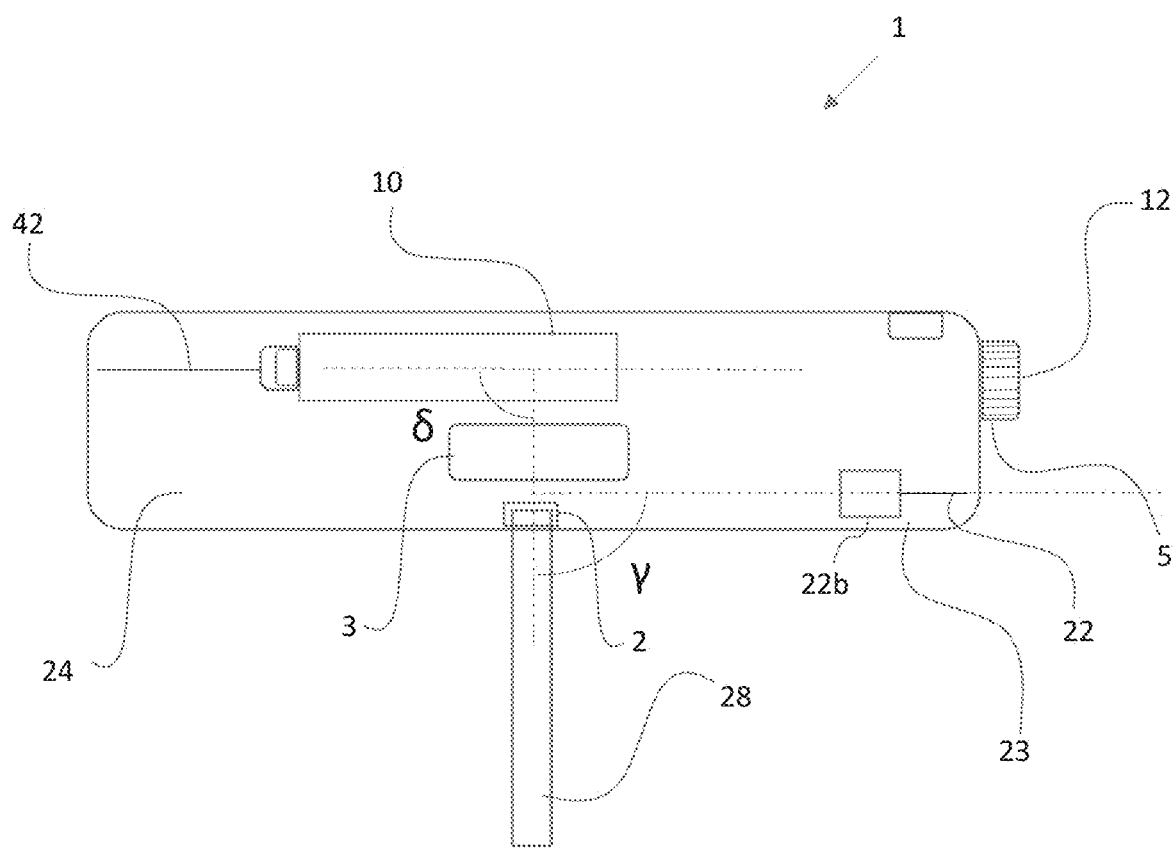

Suitably, blood glucose measurement by glucose meter 9 is automatically started when a test strip 28 is inserted into the test strip port 2. For example, a sensor senses when a test strip is introduced into the test strip port 2. An example of how test strip 28 is inserted into test strip port is shown in FIG. 13. The user then produces a drop of blood, preferably by using the lancet 22 as described below. The user then touches a drop of blood to the edge of the test strip which absorbs the blood and delivers it by capillary action along the test strip 28 to the site where the chemical reaction occurs. Typically a blood drop with a volume of 1-20 microliters is used.

By means of the integrated blood glucose meter 9 the glucose concentration is determined and indicated on the first display 3 within a few seconds, to allow the user to go to the injection mode and adjust the amount of insulin to be injected. Blood glucose measurements are usually expressed as mmol/L or mg/L and the device can suitably show the blood glucose concentration in one of these units. Preferably the user primes the injection means before setting the amount of insulin to be injected.

The means for injecting insulin comprises a cartridge housing 10 for inserting a cartridge 40 pre-loaded with insulin. The cartridge housing 10 is adapted to receive an insulin cartridge 40. The cartridge housing 10 has at least a front plate 4 that limits the movement of the insulin cartridge 40 in the direction of injection. The needle 42 in FIG. 2 and FIG. 3 can be snapped on or screwed onto the top of the cartridge 40 or connected to cartridge 40 with a luer lock or connected by other suitable means. The cartridge 40 can be replaced in a simple manner by the user.

The injection means comprises a drive mechanism 13 which causes the plunger 41 to move when the user interacts with the device to cause ejection of insulin, for example by pressing actuator 12. The drive mechanism 13 can be carried out in different manners as long as it is suitable to inject insulin from an insulin cartridge 10 in a patient and can be combined with sensors as described below.

The means for injecting insulin comprises means 5 for setting the amount of insulin to be ejected by the device (dose setting means). The dose setting means 5 can be a rotatable dosing knob 5, but it can be any type of means by which the user can instruct the drive mechanism 13 of the injection means of device 1 to change its dose setting. For example it may be a plus/minus buttons or a lever. The rotatable dosing knob suitably has grooves for enhancing the grip. The amount of insulin to be ejected by the device 1 is shown on a display 6, referred to as the second display 6, which is described in more detail below. The dose setting means 5 is connected to, and may form a part of the drive mechanism 13. The drive mechanism 13 can cause the plunger 41 to be displaced thus creating a pressure in insulin cartridge 40 in the cartridge housing 10 by pressing on second plunger 45 in the cartridge 40. The pressure causes ejection of insulin trough the needle 42 connected to the cartridge 40. The drive mechanism 13 can cause the plunger 41 to be displaced to in a variable manner. The setting of the dose setting means 5 determines how far the drive mechanism 13 displaces plunger 41 during ejection.

The dose setting means 5 should have at least one setting that does not allow the ejection of insulin. When the dose setting means 5 is in this position no insulin is ejected when the user instructs the device to eject insulin, for example when the user applies pressure to the actuator 12. Thus, the plunger 41 does not move when the user presses the actuator 12 when the dose setting means 5 is in this position.

The dose setting means 5 should have at least one setting that allows the ejection of insulin from the cartridge, for example a fixed amount of insulin. Typically the settings for the second display 6 are 0, 1.0, 1.5, 2.0, 2.5 and so on representing insulin units, where one unit may represent 0.01 ml of medicament. The "0" setting is a setting that does not allow ejection of insulin. The settings 1.0, 1.5, 2.0, and 2.5 are settings that allow the ejection of insulin.

The means for injecting insulin also comprises an injection actuator 12. This may be in the form of knob that is pressed by the user. The dosing knob and the injection actuator may be integrated in the same unit such that the rotatable dosing knob 5, 12 can be depressed, and when it is depressed ejection takes place.

The drive mechanism 13 for ejecting insulin can be an electric pump. Preferably, however, it is a user-powered drive mechanism. Examples of user powered mechanical drive mechanism and dose setting means and mechanical displays are disclosed in U.S. Pat. Nos. 5,593,390, 6,221,046, 5,279,586 and WO2009027950.

The drive mechanism 13 can be powered by the user such that when the user uses the actuation means 12 the power is transferred to the drive mechanism 13. The amount of insulin to be ejected is set by turning the dose setting means 5 so that mechanism 13 can move plunger 41 to eject insulin from cartridge 40 and the dose setting means 5 determines how far the plunger 41 travels.

Figure 7:
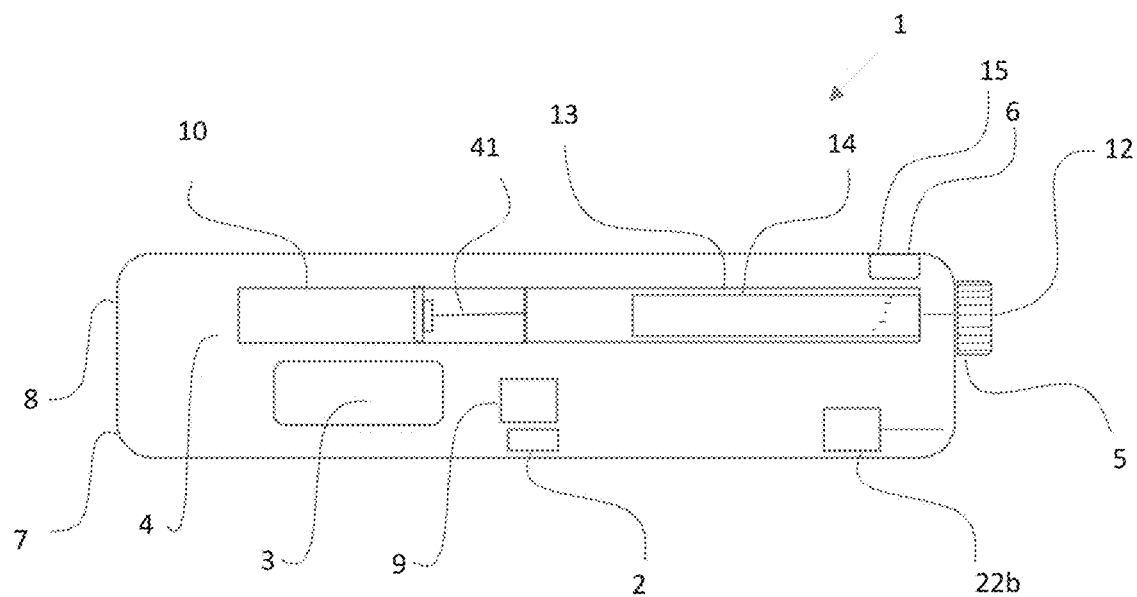
FIGS. 7-9 are examples of an arrangement of the second display, where
Figure 25:
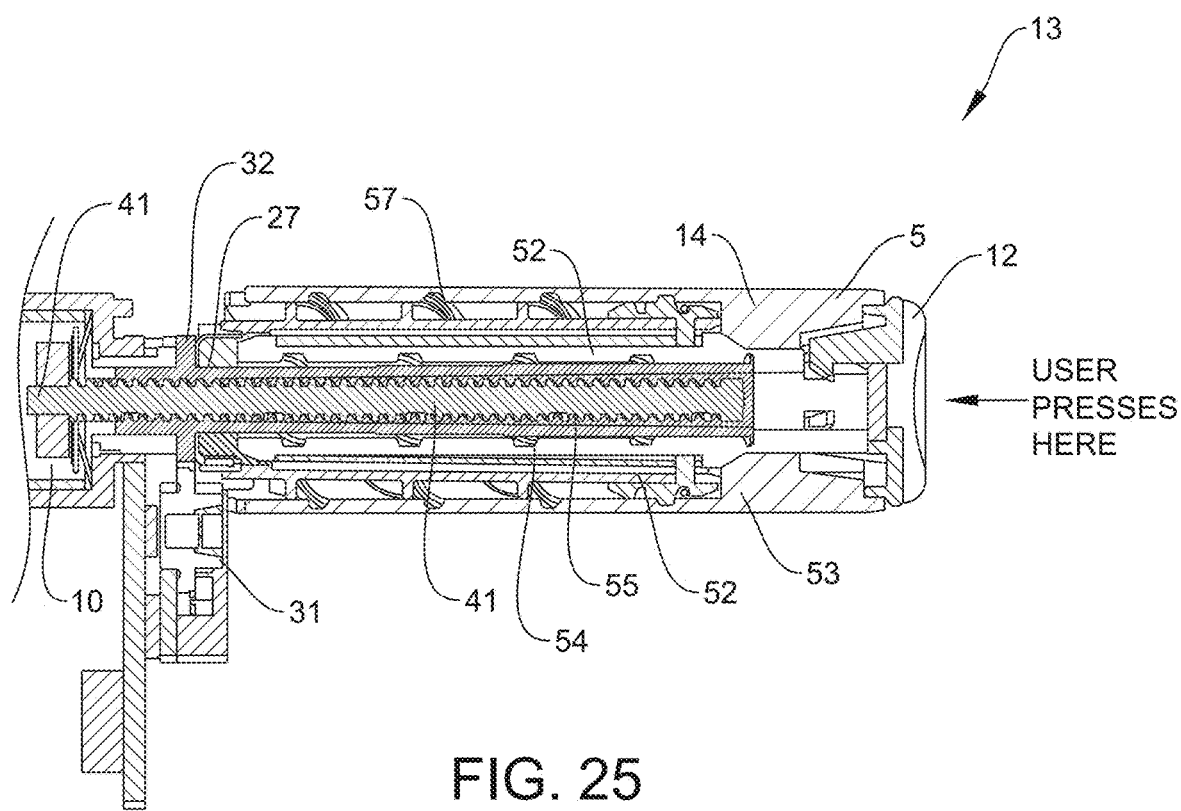
FIGS. 25-27 shows details of an example of a drive mechanism of injection means.

An example of a user powered drive mechanism and a mechanical display is shown in FIG. 25. The mechanism is shown when set in a position that does not allow injection of insulin. Sleeve 14 serves to display the dose setting digits to the user and to interact with switch 18 as described below. Sleeve 14 has dose settings marked on the outside. These marking is visible to the user, for example through a window as seen in FIG. 7. Sleeve 14 can rotate with turning of dose setting means 5. When a user rotates dose setting means 5 to set the dose, sleeve 14 rotates with it. Sleeve 14 then moves to the right in the figure due to threading 57. Nut 52 rotates together with sleeve 14 by means of cone clutch 53. This makes the nut 52 go to the right in the figure. The movement of nut 52 from its left-most position sets the injection means to a setting that allows the injection of insulin.

When the user has set the dose he or she is not ready to eject insulin. The injection actuator 12 is connected at the end of the sleeve 14. The injection actuator 12 can be pressed by the user. The arrow in FIG. 25 indicates direction of pressing. Upon pressing the injection actuator 12 then moves to the left in the figure. The outer surface of injection actuator 12 is covered with a material (for example rubber) that causes high friction between the finger of the user and the injection actuator 12. When the user presses the injection actuator 12, the nut 52 is released from sleeve 14 by cone clutch 53 and moves to the left to the same extent that the injection actuator 12 is pressed. Injection actuator 12 then, subsequently, presses on sleeve 14 which turns with aid of threading 57 and moves to the left. Release of cone clutch 53 is achieved by gap 58. Gap 58 causes injection actuator 12 to first press on nut 52 and then, after being presses slightly more, on sleeve 14, causing cone clutch 53 to be released. Nut 52 is not allowed to turn when pressed by injection actuator 12 because of the high friction between the finger of the user and the outer surface of injection actuator 12 and because the cone clutch 53 is released. Nut 52, however, moves to the left when injection actuator 12 is pressed. This movement continues until the right end (in the figure) of the turning part 27 has reached the inner surface 56 of the injection actuator 12. This movement of nut 52 causes turning part 27 to turn inside it with the aid of threading grooves 54 and to feed threaded plunger 41 to the left with the aid of threading 55. Thus plunger 41 does not turn. A comparatively large movement of injection actuator 12 is thereby geared to a much smaller movement of plunger 41 due to different steepness of threading 54 and threading 55.

Figure 26:
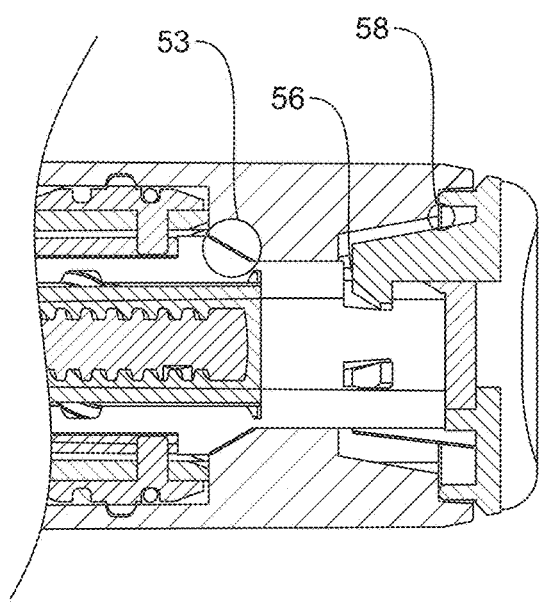
Figure 27:
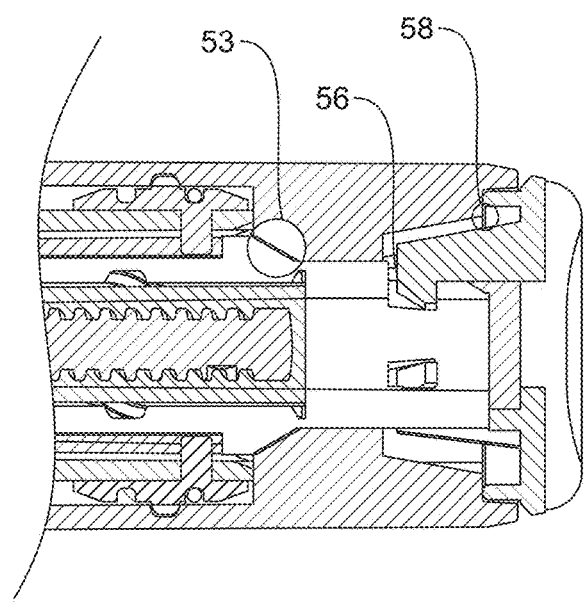

Turning part 27 feeds plunger 41 towards the left and causes ejection of insulin each time user presses the injection actuator 12 (presuming that the dose injection means 5 is set to a setting that allows the ejection of insulin). Plunger 41 is returned to the starting position when the cartridge 40 is replaced. FIG. 26 and shows the cone clutch 53 in its engaged state and FIG. 27 shows the clone clutch in its disengaged state.

The drive mechanism 13 can be combined with a deactivation means that suitably comprises at least one sensor for sensing movement or settings of the drive mechanism 13, or dose setting means 5. In general, sensors that are capable of detecting movement in a mechanism or the setting of a mechanism are well known. The sensor may be a position sensor, such as setting mean sensor 17 that senses the position of a part of drive mechanism 13. In particular the setting mean sensor 17 may sense the position of a part of a drive mechanism 13 that changes position as the setting of the dose setting means 5 changes. The part of drive mechanism being sensed by setting mean sensor 17 is preferably a part, the position of which, is determined by the setting of dose setting means 5. An example of such a part of drive mechanism 13 is member 29 of sleeve 14. The at least one sensor is connected to and arranged to communicate with processing unit 19.

Preferably the device has a deactivation means comprising a sensor 17 that can sense when the dose setting means 5 is set to a setting that permits the drive mechanism to eject insulin as is described below. The deactivation means which is an important part of the invention is described further below, as it can be used to switch off first display 3.

The device 1 has a user interface that includes one or more displays, buttons for navigation in menus, and an input device for entering input. The user can obtain information such as status of the device, blood glucose measurements and the setting of the dose setting means 5 from at least one display.

In a preferred embodiment, however, the device 1 has at least two displays: a first display 3 and a second display 6. In this embodiment the purpose of the second display 6 is mainly to show the setting of the dose setting means 5, thus to show the amount of insulin to be ejected. In a preferred embodiment the second display 6 only displays the setting of the dose setting means 5. Other information such as blood glucose measurements, are shown on the first display 3. In particular, the blood glucose measurements are shown on the first display 3. In one embodiment the device has one mechanical display (second display 6) that is capable of showing the amount of insulin to be ejected by the device and at least one electronic display (first display 3) capable of showing blood glucose measurements. A mechanical display preferably works without being powered, for example by electricity. Thus it can display the dose setting (the amount of insulin to be ejected) without being powered.

Figure 23:
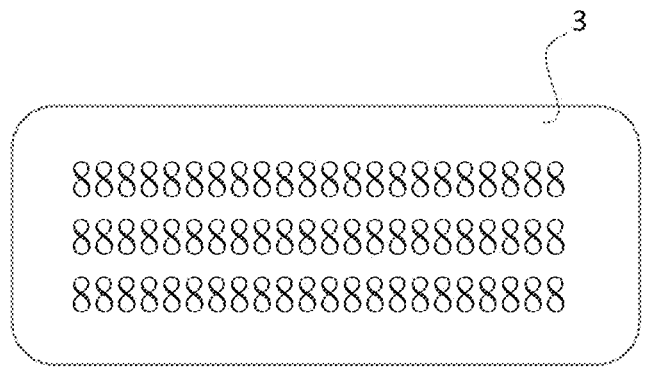
FIGS. 23-24 shows examples of an electronic display in a switched-off state.
Figure 24:
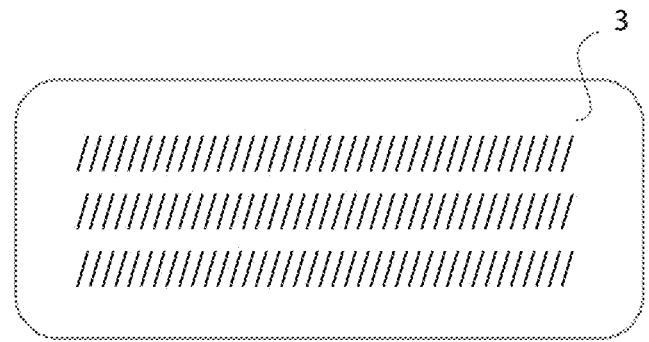

The first display 3 can be either switched on or switched off. For purposes of this application, "switched on" means that the first display 3 is capable of showing letters and numbers, for example a blood glucose measurement, and "switched off" means that the first display 3 does not shown any letter, digit or symbol that can be confused with a letter or a digit of a blood glucose measurement. For example, the first display 3 can show lines or circles or other figures that have a low probability for being mistaken for an actual blood glucose measurement; and still be considered to be switched off. This indicates to the user that the first display 3 is not broken but merely that it is currently not displaying any information. For example, if most of the display shows several rows of dashes (as in FIG. 24) it will considered to be switched off. Also, for example, if the first display 3 shows several rows of the same digit, for example the digit "8" (as in FIG. 23) it will also be considered be switched off, since this will probably not be mistaken for an actual glucose reading or an injection event. The deactivation means off course also switch off the first display 3 by causing the processing unit 19 to cut the power to the first display 3. I will then not be able to show any letter, digit or symbol.

Figure 8:
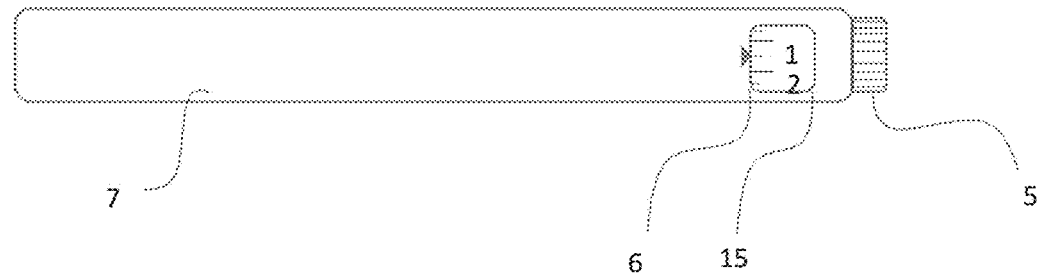
Figure 9:
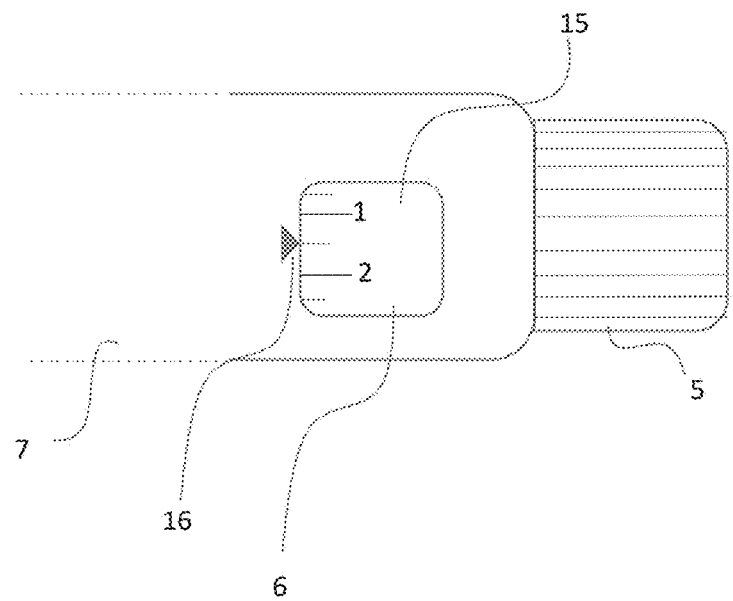

FIGS. 7-9 shows one way of arranging the second display 6 when it is a mechanical display. Here the second display 6 is arranged on a short side of the device 1. Sleeve 14, which is a part of drive mechanism 13, rotates with the dose setting means 5, the sleeve 14 having dose markings on the outside. The dose marking may be written in a spiral-like fashion on outside of sleeve 14 since the sleeve 14 may move when the dose is set. Sleeve 14 is arranged in the housing 7 such that a section of the sleeve 14 is visible through a window 15 in the housing 7, as shown in FIGS. 7-9. FIG. 8 shows the second display 6 seen from above and FIG. 9 is an enlargement of FIG. 8. The sleeve 14 is connected to the dosing knob 5 such that the sleeve 14 rotates when the dosing knob 5 is turned. The selected dose is shown in the window 15 indicated by an arrow or line 16 on the housing 7. The setting of sleeve 14 determines the amount of insulin to be ejected by drive mechanism 13 (as it determines how far 52 moves to the right in FIG. 25 nut). The second display 6 may also be such that all the figures are visible and that the selected number is indicated by a line or an arrow.

In a preferred embodiment the first display 3 is automatically switched off by a deactivation means, that may include, for example a position sensor, when the dose setting means 5 is set to a setting that permits the ejection of insulin. Thus, the first display 3 is switched off when the dose setting means 5 it set to—for example—1.0, 1.5, 2.0, 2.5 and so on, but active or switched on when the dose setting means 5 is set to the at least one setting that does not allow ejection of insulin, such as 0 (zero) or any other setting that results in that no insulin can be ejected. For example, besides the setting 0 (zero) there may also be an "off"-setting that also inactivates the insulin injection means, and that allows the activation of the first display 3.

This arrangement directs the attention of the user to the second display 6 which shows the amount of insulin to be ejected. This reduces the risk that the user sets the wrong value of the dose setting means 5. For example, there is no risk that the user looks at the blood glucose measurement and believes that the value of the blood glucose measurement is the dose to be ejected. Furthermore it directs the user to take the next step in the procedure and complete that step and not backtrack to the previous step (which is the blood glucose measurement step). Thus, the user is guided towards taking the next step in the procedure.

Figure 10:
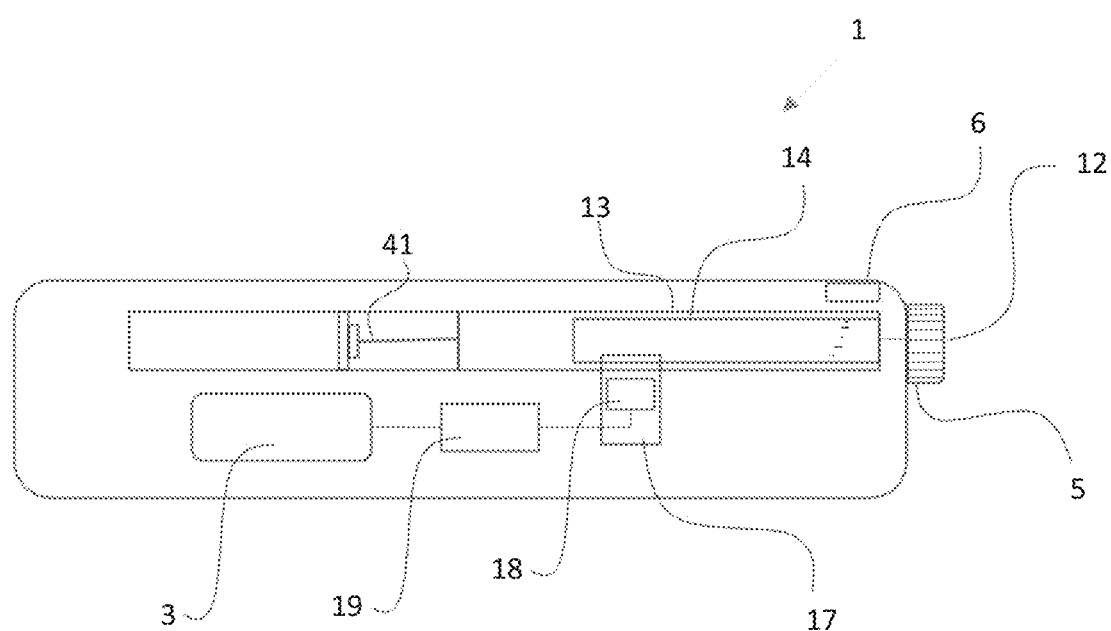
FIG. 10 is a schematic overview of the connection of a sensor to a processing unit.

A schematic diagram of an example of the deactivation means of the device is shown in FIG. 10. When the dosing knob 5 is turned, a setting mean sensor 17 which may comprise a switch 18 sends a signal to a processing unit 19 which switches off the first display 3. The setting mean sensor 17 may for example comprise a spring that causes a member to push on a turning part of the dose setting mechanism of the drive mechanism 13, said member moving a switch 18 when the member enters a groove in the turning part of the dose setting mechanism. The groove is positioned such that the member can enter the groove only when the dose setting knob 5 is set to the at least one setting that does not permit ejection of insulin, for example a zero setting.

Figure 6:
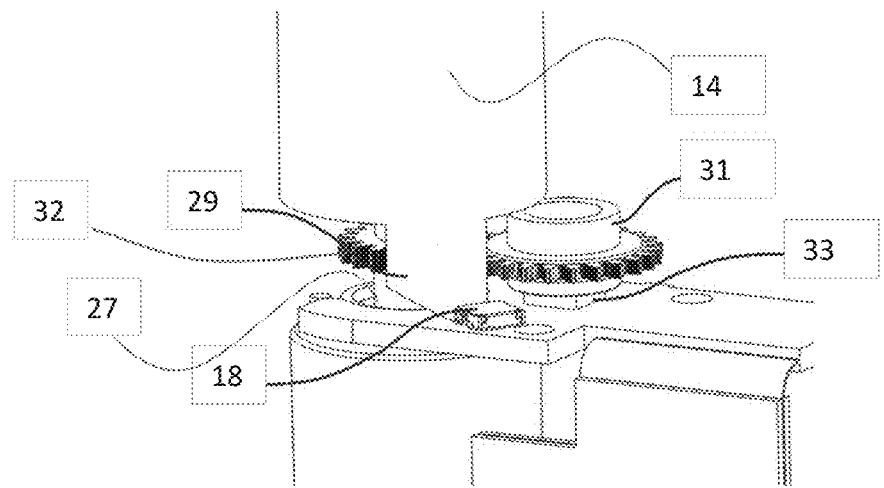
FIG. 6 shows an example of arrangement of sensors.

Another example of such a setting mean sensor 17 is shown in FIG. 6 which shows a detail of the mechanism of FIG. 25. Switch 18 is arranged to detect downward and turning motion of sleeve 14 which sets the amount of insulin to be ejected. When sleeve 14 is in its most downward position the drive mechanism 13 is set to zero and member 29 of sleeve 14 is in contact with switch 18. The causes the first display 3 to be switched on. When the user turns the setting knob 5 to set an amount of insulin to be ejected sleeve 14 turns and moves upward in FIG. 6 so that member 29 releases switch 18 which sends a signal to processing unit 19. This signal causes the first display 3 to be switched off.

The deactivation means can be arranged in many other ways. For example a semiconductor accelerometer of the type used in cell phones (smart phones) can be used for sensing the movement or position of a part of drive mechanism 13.

The dose setting means of the user-powered drive mechanism of U.S. Pat. Nos. 5,593,390, 6,221,046 and WO2009027950 can be easily adapted by a person skilled in the art to be sensed by setting mean sensor 17 and ejection sensor 33. Those are examples of injection means that can be used in embodiments of the invention. For example, U.S. Pat. No. 5,593,390 discloses an injection means with cam lobes that affect a counter that can serve as the sensor 33.

The device can be such that the first display 3 is automatically reactivated when the dose setting means 5 is set to zero. This is a convenient manner for the user to reactivate the display if necessary, for example if the user has forgot the blood glucose value and must re-check this. At the same time it forces the user to set the value of the dose setting means to zero if he or she needs to switch on the first display. This can be achieved by setting mean sensor 17 sensing that the dose setting means 5 is set in a position that does not permit the ejection of insulin. As discussed above, when the user sets the dose setting means 5 to zero, sleeve 14 is its most downward position in FIG. 6. When sleeve 14 is in this position, member 29 is in contact with switch 18 and this sends a signal to processing unit 19 which causes first display 3 to be switched on.

In one embodiment the first display 3 is automatically switched on when ejection of insulin has been completed. With reference to FIG. 25 and FIG. 6, the dose setting means 5 returns to the zero setting during ejection. The switching on of first display 3 can be achieved by setting mean sensor 17 sensing that the dose setting means 5 has returned to the zero setting during ejection. With reference to FIG. 6 and FIG. 25 sleeve 14 move s downward during ejection of the medicament so that member 29 reaches switch 18 when actuation means 12 is depressed so that the zero setting is reached. Thereby, the first display 3 is automatically switched on. This enables the user to tag the injection event as described below if he or she wishes to do so. Again, the attention of the user is directed to the next step in the procedure which is using the first display 3 to log the injection event.

In one embodiment the first display 3 and second display 6 are not visible at the same time by the user, such that the user cannot read the first display at the same time as the second display. An advantage with this arrangement is that the user can not confuse the values on the two displays. The two displays 3, 6 can, for example, be geometrically arranged such that it is only possible to see one display at a time. Alternatively one display can be of a kind where the digits are only visible from a certain angle.

Figure 11:
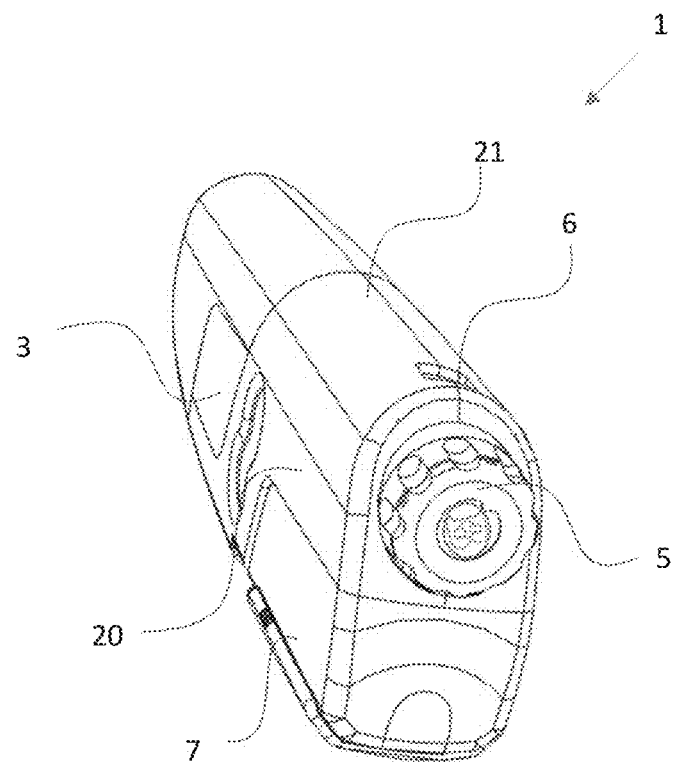
FIGS. 11-13 show examples of arrangement of first and second displays and other features of the device.
Figure 12:
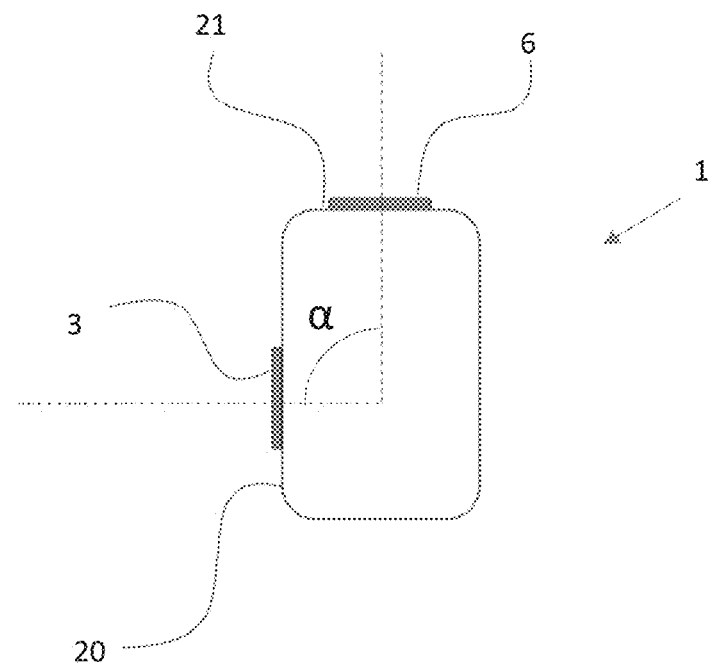

Preferably the displays 3, 6 are on different surfaces on the housing of the device as shown in FIG. 11-12 where the first display 3 is arranged on a first side 20 of the housing 7 and the second display 6 is arranged on second side 21 of the housing 7. The relationship of the surfaces of the displays 3, 6 can be defined by the angles of the surfaces of the displays. FIG. 12 shows an example of an elongated housing 7 of device 1 seen from the dosing knob 5. The angle α between a line perpendicular to the surface of the first display 3 and a line that is perpendicular to the surface of the second display 6 is at least 45°, more preferably 60°, more preferably at least 70°, more preferably at least 80° most preferably at least 90°. "Line perpendicular" to the surface of display refers to a line that goes through the surface of the display on the part of the display where the indicated number, letter or symbol is visible. Typically this will be the direction from where the user most conveniently observes the display. When the angle α is 45° or more it is difficult for the user to see both displays at the same time, which reduces the risk of confusing the two displays and further directs the attention of the user/patient to one display at a time.

The device 1 can be equipped with a lancet mechanism 22b with a site for connecting a replaceable lancet 22 as shown schematically in FIG. 1 and FIG. 13. The lancet 22 is typically a sharp needle made of surgical grade steel that is able to make a small puncture in the skin in order to obtain a drop of blood, to be used in blood glucose measurement. Typically the lancet 22 is powered by a spring mechanism 22b and ejected after interaction by the user, for example when the user presses an actuator. Preferably the lancet 22 and its mechanism 22b is contained in the housing 7 when not in use, the tip of the lancet 22 being ejected trough a small opening in housing 7 when the user presses an actuator. The lancet 22 should be ejected with a speed that is sufficiently for the lancet 22 to puncture the skin and preferably have a stroke depth of 2-3 mm. Lancet mechanisms are well known in the art. An example of a spring mechanism for a lancet is disclosed in WO2009027950. The lancet 22 can also be powered by compressed gas. An advantage for including a lancet 22 in the device is that there are fewer loose things for the user to keep track of.

The housing 7 of the device 1 can be elongated, and roughly have the proportions as shown in FIG. 13 and FIGS. 4 and 5. Again, the size of the housing 7 is such that it can conveniently rest in the hand of the user. When the housing 7 is elongated, the lancet 22 or the site for connecting the lancet 22 is preferably located so that lancet needle is in one end 23 of the housing 7 and the cartridge housing 10 is preferably located in the opposite end 24 of the elongated housing 7 so that the needle 42, when connected, is in the opposite end 24 of the housing 7. This may also apply when the housing is not elongated. Furthermore the injection actuator 12 is preferably located on the same end 23 of the housing 7 as the site for connecting a lancet 22. This has the advantage that the user, when he or she is positioned to interact with the injection actuator 12, for example has a finger positioned to depress the injection actuator 12, he or she does not try to inject himself with the lancet 22. This provides additional safety.

When the housing 7 is elongated the first display 3 is preferably located in the middle of elongated shape as shown in FIG. 13. When the device 1 comprises a glucose meter 9, the test strip port 2 is also preferably located in the middle of the elongated shape as shown in FIG. 13. In this manner the interaction points of the user for glucose measurement is located in the middle of the housing 7 of device 1. Thus, the middle of the area of the first display 3 is located approximately 50% from the end of the housing 7. Approximately 50% includes 30% to 70%, even more preferably 35% to 65% and most preferably 40% to 60% of the distance from the end of the housing. Furthermore, the second display 6 is preferably located at one end of the housing, preferably the same end 23 as lancet 22. This further separates the first and second displays 3, 6 and mentally connects each display 3, 6 to a certain way of interacting with the device, which makes it easier to remember. It also has the advantage that the first display 3 is clearly visible when the device is held with two hands.

For further indicating the work flow and allocating the various function to different parts of the device 1 the angle β between the lancet 22, when the device has a site for connecting a lancet, and the injection needle, when connected, is preferably about 160°-220°, more preferably 170°-190°, most preferably about 180°. Thus, the lancet 22 and the injection needle 42 are pointing in different directions. Although the injection needle 42 is not a part of this invention, the direction of the injection needle 42 is determined by the direction of the cartridge housing 10.

The test strip port 2 comprises an opening in the housing 7 and an elongated tunnel which guides the test strip into the glucose meter 9. Suitably the cross section of the tunnel is somewhat larger than the cross section of a test strip so that the test strip is guided into the glucose meter 9. When the device has a lancet 22 or a site for connecting a lancet and glucose meter, the test strip port 2 is preferably arranged such that the angle γ between the test strip 28, when inserted into the test strip port 2, and the lancet 22 is from 45° to 135°, more preferably from 80° to 100°, most preferably about 90°.

When the device has a glucose meter 9 the angle δ between the test strip 28, when inserted into the test strip port 2, and the injection needle 42 is preferably from 45° to 135°, more preferably from 80° to 100°, most preferably about 90°.

The device may have an ejection sensor 33 for detecting the amount of insulin that has been ejected by the device. Ejection sensor 33 is connected to drive mechanism 13 such that it can send a signal to the processing unit 19 that is related or proportional to the amount of insulin that is ejected by the injection means of the device. An example of the arrangement of such a sensor is shown in FIG. 6 which shows a sensor which detects rotation of turning part 27 of drive mechanism 13. Turning part 27 which is a part of drive mechanism 13 has a rim which forms a cogwheel 32 to which cogwheel 31 is connected. Turning of cogwheel 31 is detected by magnetic ejection sensor 33 which is able to send a signal to the processing unit 19. When the user presses actuation means 12 the turning part 27 turns during ejection of insulin. Turing of turning part 27 causes turning of cogwheels 32 and 31. The turning of the cogwheel 31 and the signal from the magnetic ejection sensor 33 is proportional to the turning of turning part 27 and thus to the amount of insulin that has been ejected.

The medical device 1 can be equipped with a proximity sensor 35 connected to processing unit 19. The proximity sensor 35 can sense the presence of a solid object, preferably the body or a part of the body of a person. Preferably this is archived without making contact with the object. The proximity sensor should be able to detect the body of the user if the skin is bare or covered by clothing. It should also be able to detect a human body irrespectively of various skin hues.

The proximity sensor 35 can be a distance measuring sensor that sends a signal to the processing unit 19 that can be converted to a distance measurement. Alternatively, the sensor can be a binary proximity sensor such that it does not actually measure or quantify the distance but produces a detectable signal change if a solid object is within a threshold distance.

Suitably the proximity sensor 35 is arranged to send a detectable change in a signal when an object is within a threshold distance. Thus the sensor can be arranged to send a signal when an object is within the threshold distance and to cease to send the signal when there is no object within the threshold distance. The sensor may alternatively be arranged to continuously send a signal if there is no object within the threshold distance, but to cease to send the signal when there is an object within the threshold distance. The threshold distance T is defined as shown in FIG. 14; from the inside of the front plate 4 of the cartridge housing 10 and in the direction of the injection needle 42

Preferably the proximity sensor 35 reacts to an object with a certain thickness, such that it does not sense a finger or a small object that passes through the detection zone, but does react to a larger object such as the leg or the stomach of the user. Thus the proximity sensor 35 should be such that it detects the distance from the medical device 1 to the body or a part of the body of a patient that is suitable to receive an insulin injection.

Proximity sensors may be based on heat, IR (infrared light), ultrasound or radio sensing, where IR is preferred. Sensing can be based on amplitude, frequency, phase shift or shielding of the object. The desired signal may be derived in change in, for example, capacity or sensors may comprise a transmitter and a receiver. Preferably the IR sensor has a transmitter that transmits IR and a receiver that receives IR that is deflected by a solid object. LEDs are conveniently used for transmitting the IR wave. Examples of proximity sensors are disclosed in U.S. Pat. No. 8,536,507 B2 and U.S. Pat. No. 8,350,216 B2.

As discussed above, the user is instructed to prime the injections means before each injection.

The sensor 35 can be used to automatically distinguish priming events from injection events as shown in FIG. 15, FIG. 19 and FIGS. 20-22. This is based on that the user primes the injection means in the correct manner, i.e. does not prime the injection means by injecting into an object, but instead ejects so that the tip of the needle can be observed, so that the user can observe the ejection of insulin from the tip of the needle When the device 1, with the aid of the proximity sensor 35 senses that a solid object 50 is within a certain distance T it is assumed that the ejection event is an injection event and when there is no object 50 within a certain distance T it is assumed that the ejection event is a priming event.

Figure 20:
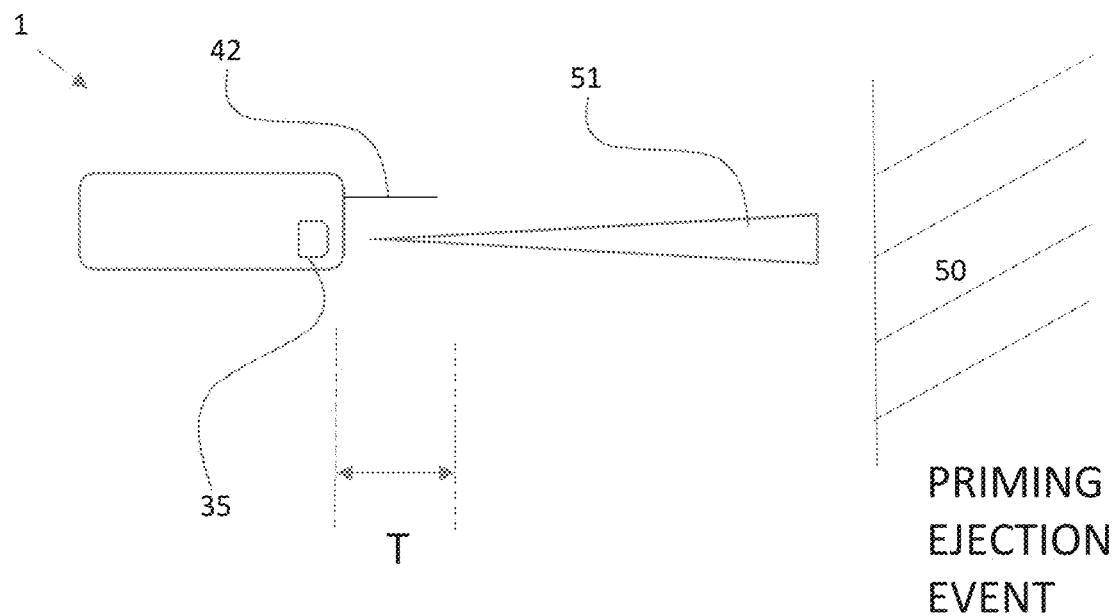
FIGS. 20-22 show how a proximity sensor can be used for classifying ejection events.

FIG. 20 is a schematic view showing device 1 with needle 42 pointed in the direction of a solid object 50. The proximity sensor 35 with detection zone 51 are also shown. In this figure the solid object 50 is not within the threshold distance T and the ejection event is logged as a priming event.

Figure 21:
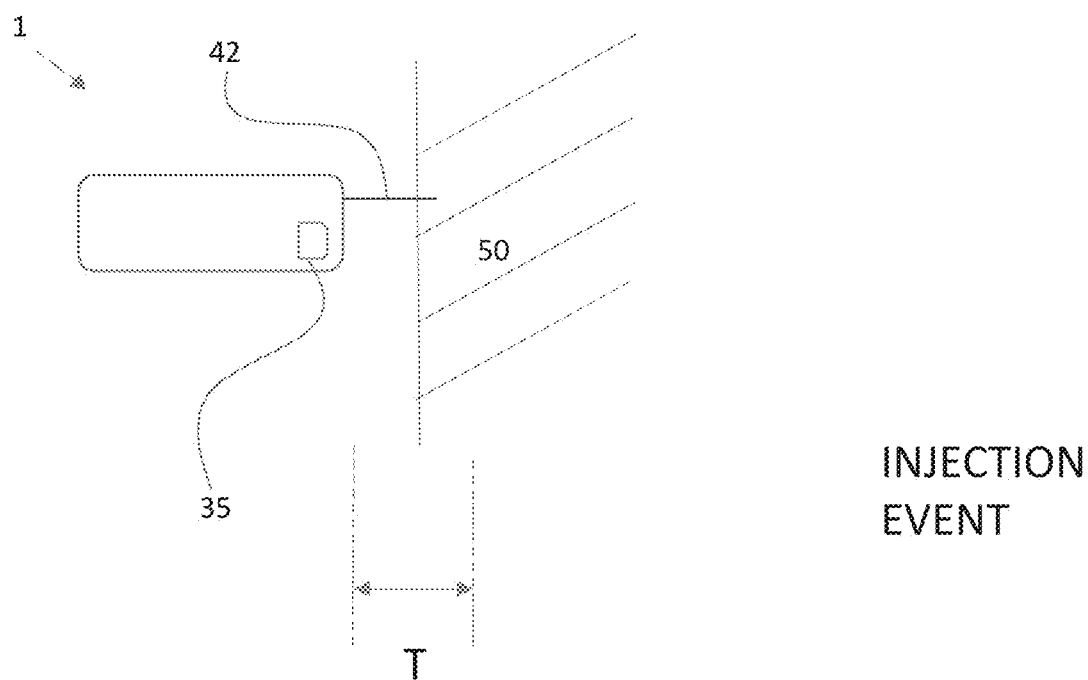

FIG. 21, shows essentially the same as FIG. 20 but here, on the other hand, a solid object 50 (the body of a patient), is within the threshold distance T and the ejection event is logged as an injection event. The detection zone is not shown in FIG. 21 for sake of clarity.

Preferably the proximity sensor 35 is arranged to transmit and receive through an opening in the housing 7. Preferably, proximity sensor 35 is placed close to the tip of the needle as practically possible, directed to sense in the direction of the tip of the needle. Sensing by the proximity sensor 35 preferably takes place approximately in the direction of the needle 42, such that it can detect when an object is in front of the tip of the needle.

The signal from the proximity sensor 35 can be used to distinguish between injection events and priming events as described below. Suitably the signal from the proximity sensor 35 is received by the processing unit 19 which can use the signal to distinguish between priming events and injection events.

Figure 17:
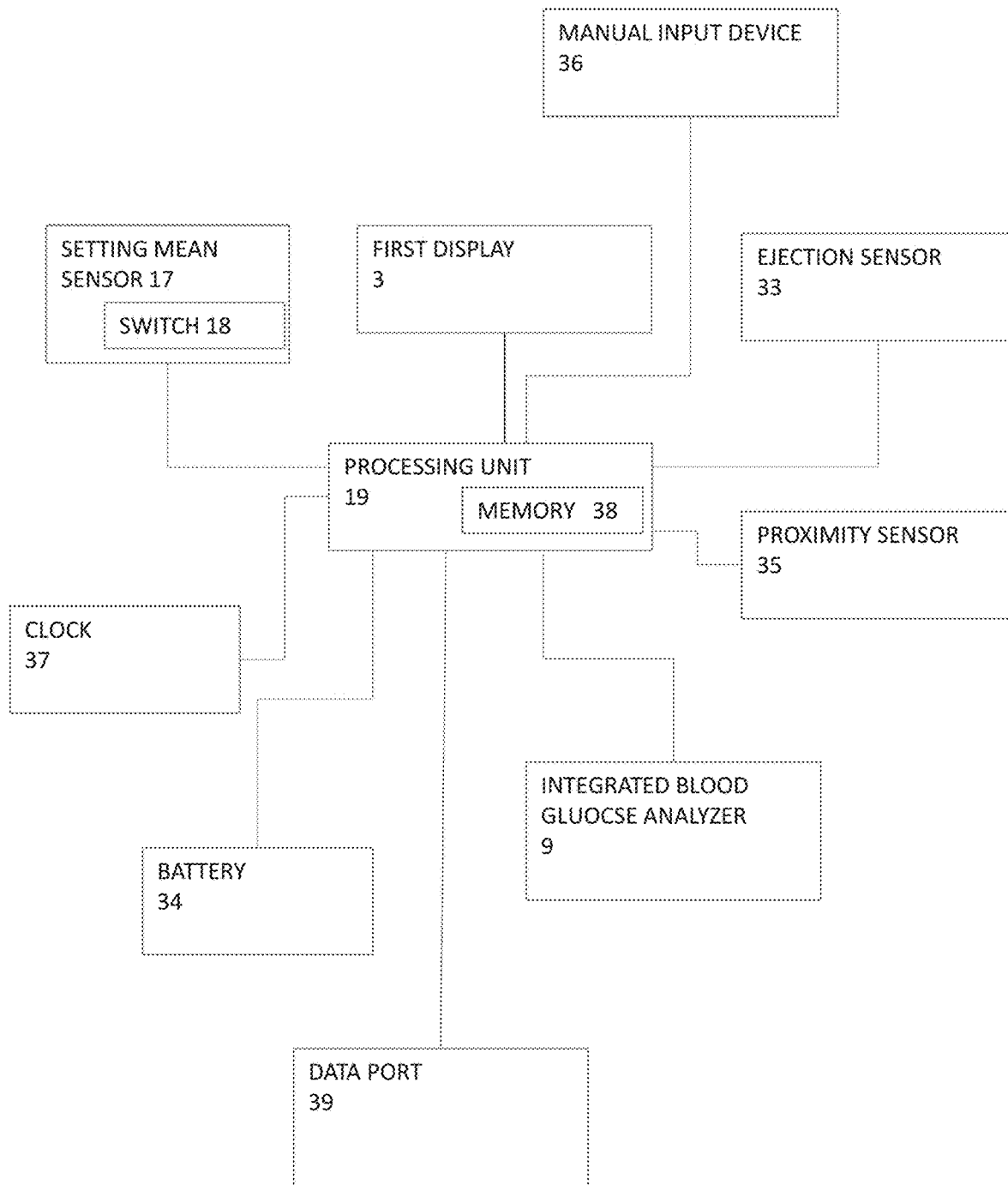
FIG. 17 shows various connections to a processing unit.

Various connections to the processing unit 19 is shown in FIG. 17. The device 1 comprises a processing unit 19 for controlling the device. The processing unit receives data from glucose meter 9, setting mean sensor 17 (which may comprise switch 18), ejection sensor 33 and proximity sensor 35. Processing unit 19 also receives input from the user and controls the first display 3. For example, processing unit 19 may store information in a database 200 that can be displayed on the first display 3 in the form of an electronic log. The processing unit 19 may be an integrated circuit, which using today's technology can have an architecture which is in the order of nanometers, e.g. as used in mobile phones. Thus the processing unit 19 does not take up much space in the housing 7. A memory 38 is also provided to allow the user to store data, for example logging injections and blood glucose measurements, preferably in the form a database 200. The processing unit 19 can also be connected through a data port 39 to a computer for extracting data and for updating any software stored on the device 1. Such a connection can be for example a USB or a micro USB connection. The data port 39 may also be a wireless connection such as a Bluetooth or a Wi-Fi connection.

The processing unit 19 may have an interface for a switch 18 of setting mean sensor 17 that detects when the dose setting means 5 is set to a setting that permits ejection of insulin.

Processing unit 19 may also have an interface for ejection sensor 33 which detects insulin ejections carried out by the insulin injection means.

The processing unit is powered by a power source such as a battery 34. Battery 34 also powers other components of the device that requires electricity such as the first display 3 and integrated glucose analyzer 9. The battery 34 can preferably be reached and replaced through a cover in the housing 7. The connection for charging may be a USB data port 39. Data port 39 also may also conveniently be used for retrieving data stored in the memory 38 of the processing unit 19.

The processing unit 19 is also connected to the first display 3 and to integrated blood glucose analyzer 9 and to proximity sensor 35.

The processing unit 19 may further have a manual input device 36 which may for example be buttons, a mini joy stick, a navigation plate or similar device for inputting data and for navigating and scrolling in menus shown on first display 3. A clock 37 provides date and time information and can also serve as a timer for the processing unit 19.

The processing unit 19 includes a memory 38, such as, for example, a flash memory, for storing software and data generated by the device 1 and by the user, e.g. the database 200. The memory 38 does not necessarily have to be enclosed in the device 1 but it can also be accessed through a wireless connection, for example a wireless network.

The database 200 can be used to log blood glucose measurements and insulin ejection events in a log so that the user, or a technician or medical staff can retrieve the events.

In a preferred embodiment the device 1 has an integrated electronic log for logging blood glucose measurements and insulin ejection events. The electronic log is essentially a database 200 stored in the memory 38 of the processing unit 19 where the database 200 is accessible through the user interface, preferably the first display 3, of the device in a convenient manner. The glucose measurement events and ejection events are stored as entries in the database 200. One schematic overview over an example of database 200 is shown in FIG. 16.

By way of example, the user, a technician or medical staff can access the electronic log by choosing an appropriate command in the menu by scrolling through the display using +/- buttons and then see a list of blood glucose measurements or ejection events, or both. Preferably the default is that the events are shown in date order with the most recent event shown first. Ejection events and glucose measurement events can be tagged by the user with additional information, that is, additional information regarding the events may be stored in the database.

Figures 15, 16:
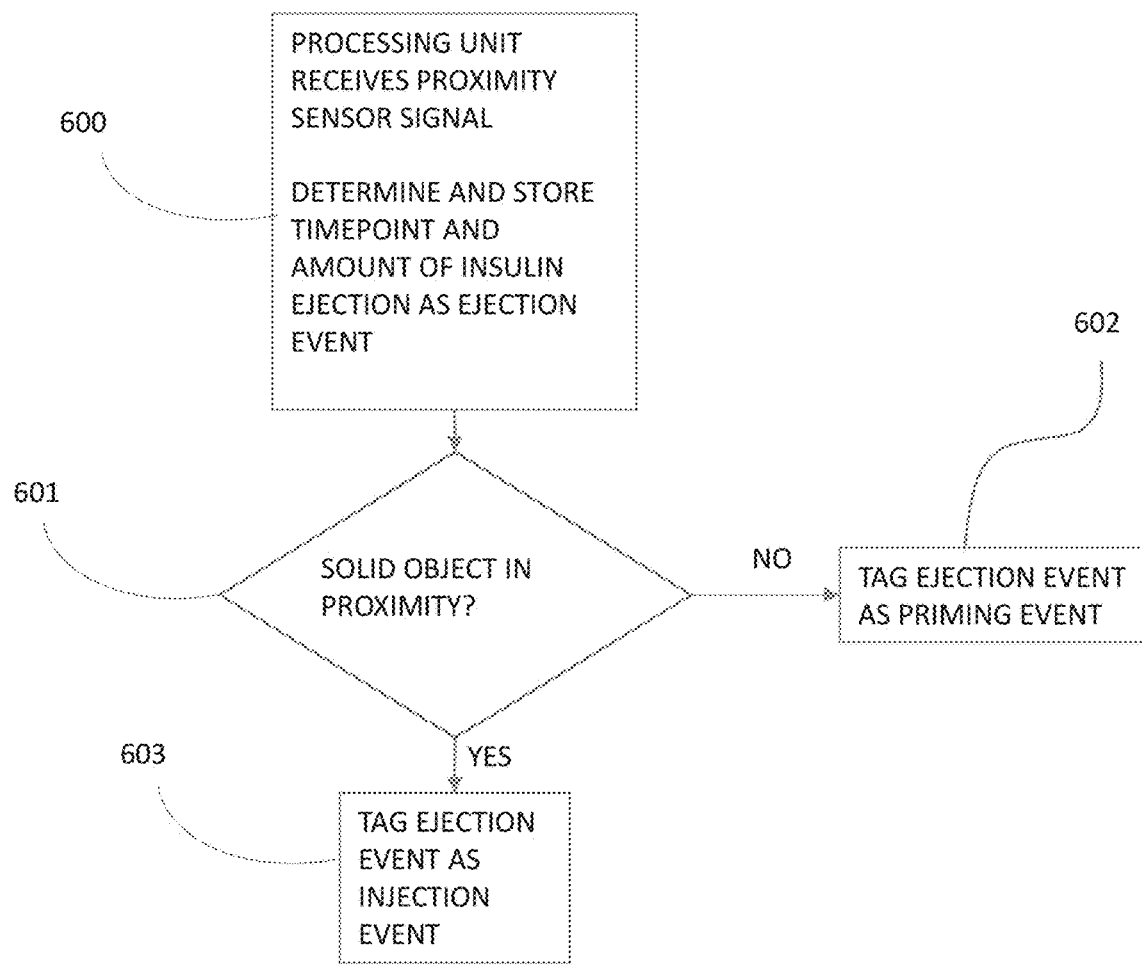
FIG. 15 is a flowchart showing a method for logging insulin ejection events.
FIG. 16 is a schematic overview of an example of database.
Figure 18:
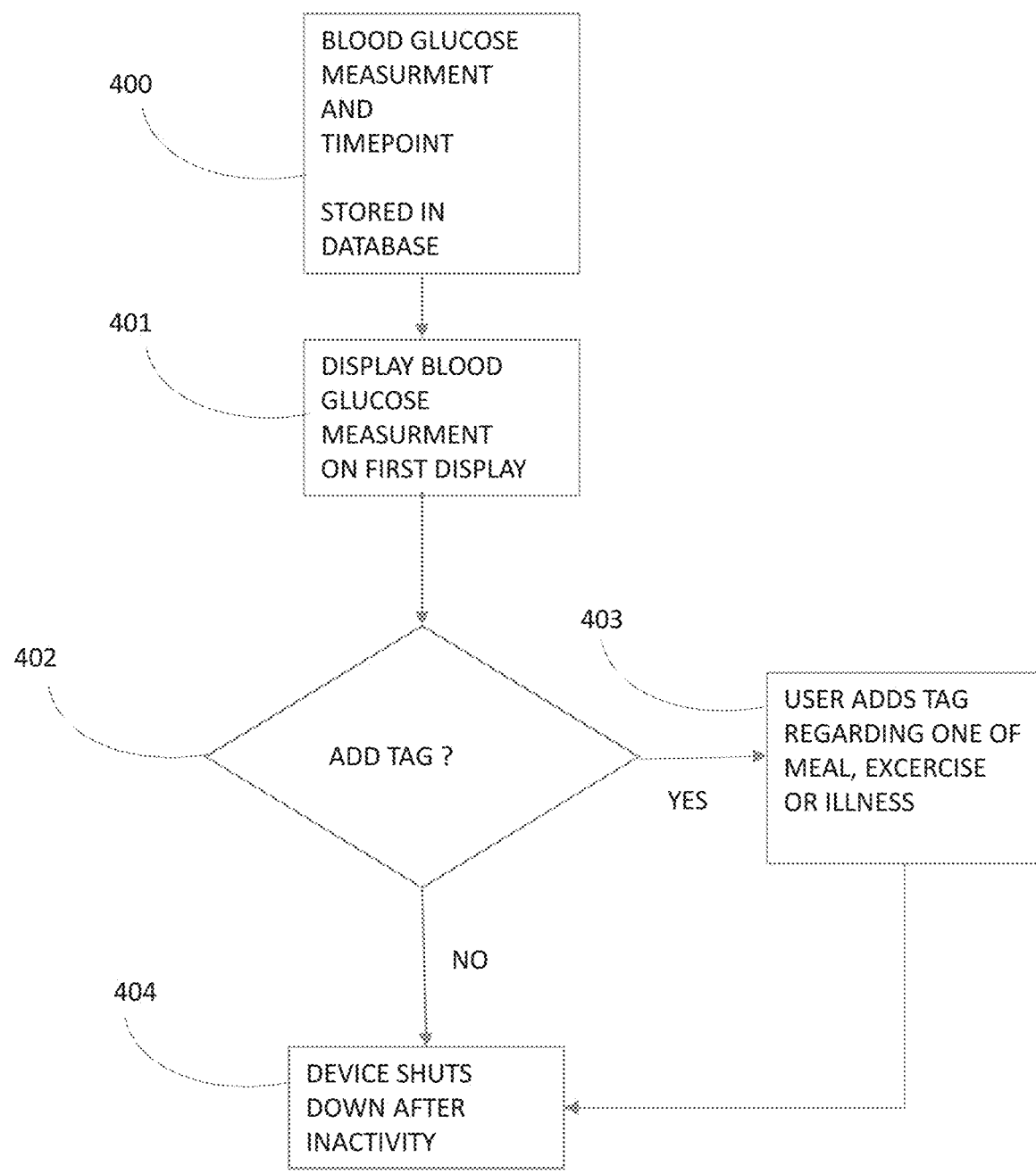
FIGS. 18-19 are flowcharts that show examples of logging of blood glucose measurements and ejection events.
Figure 19:
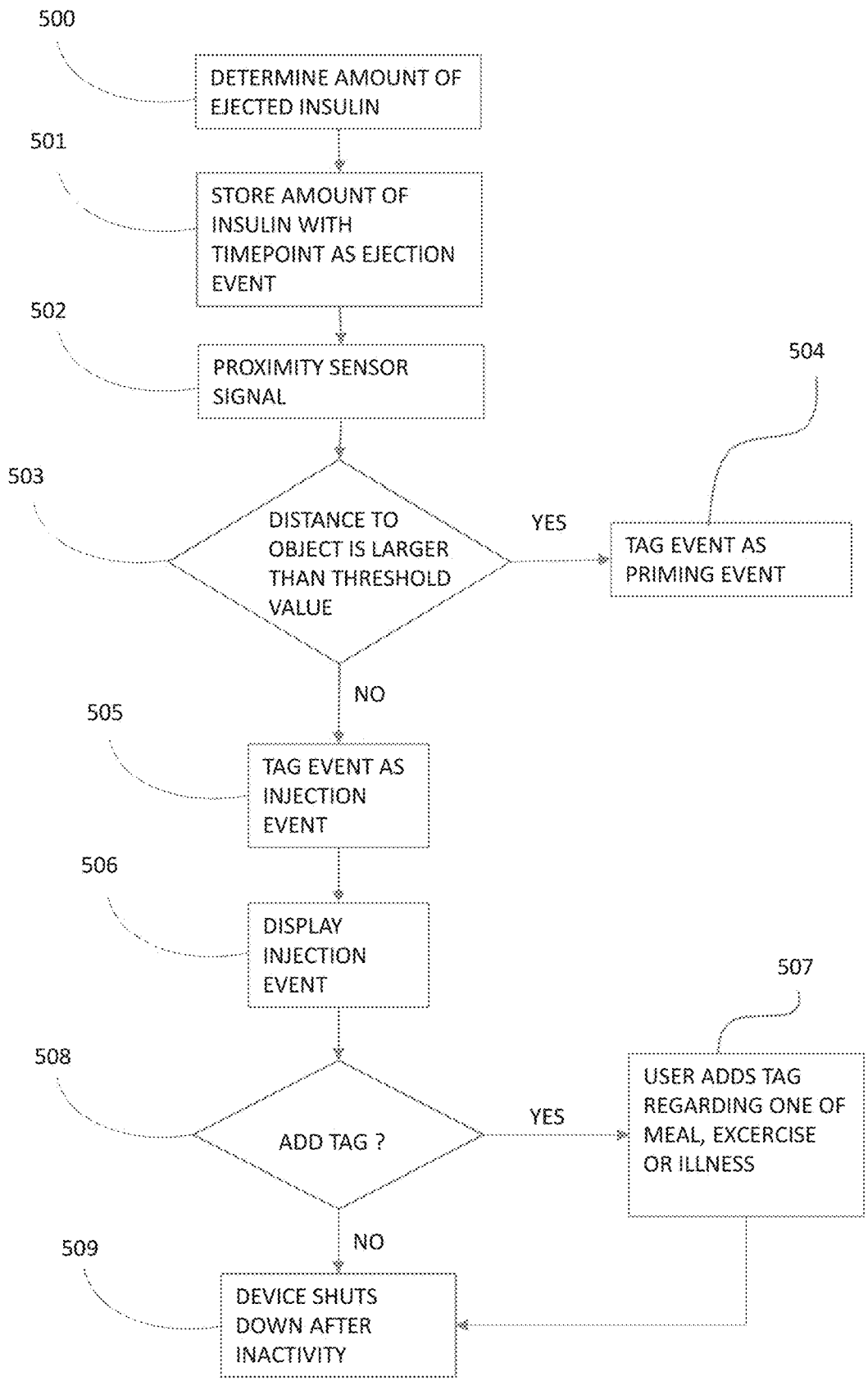

FIGS. 15, 18 and 19 are flowcharts showing examples of how the processing unit 19 and sensor 35 operates when the user carries out treatment and logs events according to the method for logging according to the invention. The steps shown in FIGS. 15, 18 and 19 are under the control of software programs stored in the memory and executed by the processing unit in a conventional fashion. Any suitable programming language or technique can be used to implement the database and the electronic log.

In its most general form the method for logging injections of a medicament is an implementation of the method schematically shown in FIG. 15. The electronic log comprises a database 200 which is stored in the memory 38 of processing unit 19. In step 600 an ejection event is stored in the memory of the device 1, the ejection event comprising information about the amount of ejected medicament and the time and date for this. During or immediately after the ejection process, the proximity sensor 35 senses if there is a solid object 50 in the proximity in the direction of the injection needle. Also in step 600, the processing unit 19 receives a signal from the proximity sensor 35. If there is no solid object in the proximity, for example if a threshold value for the distance to a solid object is exceeded, a decision is made by processing unit 19 in 601 to tag the ejection event in the memory as a priming event in 602. If there is a solid object in the proximity, the ejection event is tagged as an injection in step 603.

Preferably the method is carried out automatically by the device 1. The determination in step 601 can be carried out in different manners. In the case when the proximity sensor 35 sends a signal that can be converted to a distance measurement, the signal may be processed by the processing unit 19 which has stored the threshold value and compares the signal with the threshold value and makes the decision in 601. In the case of a binary proximity sensor, the proximity sensor 35 itself determines if there is a solid object within the threshold distance and sends a signal regarding this to the processing unit 19.

In a preferred embodiment, the threshold distance T can be set in relation to a position that is fixed in relation to the injection needle, preferably the front plate 4 of the of cartridge housing 10. The threshold distance T is measured from the inner surface of the front plate 4 to the longest distance where a solid object, such as a human body, causes a change in a signal that makes an ejection event to be classified as a priming event can be seen in FIG. 14.

The user is normally instructed to prime the injection means by holding the injection means vertically with the needle pointing upward and then ejecting a small amount of medicament while observing that medicament is ejected from the needle in a normal fashion, i.e. so that no air is left in the needle and that the needle is not blocked. Thus in normal use, it is not likely that priming ejections are made with the needle close to a solid object.

Suitably T is chosen so that it accommodates most needle lengths (including the needle hub) while still being short enough so that no erroneous logging takes place, for example, if the user holds the device under a lamp while priming. Needles for injecting insulin are usually between 4 mm and 13 mm long. Thus if an injection is made when there is no solid object within 200 mm, 100 mm, 50 mm, 40 mm, 30 mm, 25 mm, 20 mm, 18 mm, or 15 mm from the front plate 4 it is highly likely that the ejection event is a priming ejection. These distances accommodates most cartridges, length of injection needles and length of needle hubs.

The measurement of proximity sensor 35 can preferably be carried out very quickly (under 1 second) and can be carried out at any time during the ejection, or immediately after ejection. Sensor measurement should be carried out at least once during ejection, or immediately after injection, that is within 1 second of completing ejection, more preferably within 0.5 seconds of completing ejecting, as determined by ejection sensor 33. Alternatively it is carried out several times during ejection in which case it may be enough for a solid object to be within the threshold distance once during ejection as determined by ejection sensor 33 in order for the ejection event to be classified as an injection event.

Suitably ejection sensor 33 can be used to determine the time window for when ejection takes place. Thus, an ejection event may be logged as an injection event only if a solid object is within the threshold distance during the time when ejection takes place as determined by ejection sensor 33, or immediately thereafter. Thus if a solid object is within the threshold distance only after ejection has ceased as determined by ejection sensor 33, the ejection event is not logged as an injection event.

Ejection sensor 33 may activate proximity sensor 35, for example by sending a signal to proximity sensor 35. Such a signal can be sent via processing unit 19, or directly from injection sensor 33 to proximity sensor 35.

Alternatively proximity sensor 35 may be switched on by setting mean sensor 17 (preferably via processing unit 19) when setting mean sensor 17 detects that the setting means 5 is set to a setting that allows the ejection of insulin. In this case, the time window for detecting proximity may be determined by ejection sensor 33 as described above.

In the following it is described with reference to FIGS. 18 and 19 how the user can use the electronic log to log glucose measurements and medicament ejection events.

A user initializes a test by introducing a test strip 28 into the test strip port 2. This can be detected by the integrated blood glucose analyzer 9 which then automatically switches on the device. Alternatively, the user switches on the device manually by using manual input device 36. The processing unit 19 may then carry out a system check to see that the device 1 is working properly, and for example check that there is sufficient batter power to carry out the subsequent steps. Suitably, the first display 3 is then switched on, indicating to the user that the device is ready for a blood glucose test. Suitably the display 3 at this step displays text that instructs the user to introduce a blood sample such as "AWAITING BLOOD SAMPLE". The user then takes a blood sample, suitably by using the lancet 22, and places a drop of blood on the test strip. If this is not done within a suitable time frame, such as 5 minutes, the program in the processing unit 19 may shut down the device 1 in order to save battery. When a blood sample is introduced, the integrated blood glucose analyzer 9 can automatically detect this and produce a blood glucose measurement. Since it takes time to do this, the processing unit 19 suitably indicates to the user on the first display 3 that blood glucose measurement is in process, for example by counting down a timer or showing the text ANALYZING. Usually, 5 seconds is sufficient to analyze the blood sample. The device may then display an instruction to withdraw the test strip 28 from the test strip port 2. The blood glucose measurement is stored in the database 200 in the memory 38 of the processing unit together with date and time for the analysis, as a blood glucose measurement event in step 400. Then the blood glucose value is displayed on the first display 3 in step 401. The user may now be given the opportunity, in step 402, to store additional information together with the blood glucose measurement event in the database 200 in step 403. This can include adding a data point that indicates one of the following: if the user recently has taken a meal, if the user recently has carried out exercise, or if the user is feeling ill. This procedure is referred to as "tagging" the blood glucose measurement event. For example by scrolling in the menu, the user first selects "TAG" and then one of "MEAL", "EXERCISE" and "ILLNESS". If the user chooses in step 402 not to add a tag, the device 1 can automatically switches off in step 404 after a certain time of inactivity, for example 10 seconds.

The blood glucose measurement events and ejection events in the database 200 can be accessed at any time by the user, technician or medical staff. This can be done, for example, by starting the device 1 and selecting a command, for example "LOG" in the menu. The user can read the various blood glucose measurement events as a list by scrolling through the menu. Suitably, the database 200 can also be accessed through the data port 39, so that the contents of the database 200 can be transferred to a PC, tablet computer or other computing device.

Insulin ejection events can be stored in the database 200 in the following manner. In step 500 of FIG. 19 the processing unit 19 detects an insulin ejection and determines the amount of insulin that was ejected. This can be achieved by the ejection sensor 33 sending a signal to processing unit 19.

When the injection means are designed with setting mean sensor 17 the processing unit 19 may use a signal from setting mean sensor 17 to be ready to receive input from ejection sensor 33 as follows: When setting mean sensor 17 sends a signal to the processing unit 19 that the dose setting means is set to a setting that permits the ejection of insulin, processing unit 19 is set in a state so that it is ready to receive a signal from sensor 33 and sensor 33 is set in a state where it is ready to create and send a signal to processing unit 19. Thus ejection sensor 33 can be activated by setting mean sensor 17.

The signal from setting mean sensor 17 may also be used by processing unit 19 to be ready to receive input from proximity sensor 35 as follows: When setting mean sensor 17 sends a signal to the processing unit 19 that the dose setting means is set to a setting that permits the ejection of insulin, the processing unit 19 is set in a state so that it is ready to receive a signal from proximity sensor 35 and proximity sensor 35 is set in a state where it is ready to create and send a signal to processing unit 19. Thus proximity sensor 35 can be activated by setting mean sensor 17.

Information about the amount of insulin that has been ejected is stored in the memory 38 of the device, preferably in the database 200, as an ejection event together with date and time for ejection in step 501.

In step 502 the proximity sensor 35 senses whether ejection takes place in the proximity of a solid object. The proximity sensor can be configured to continuously measure proximity during the time of ejection, and the fact that step 502 is after step 500 and 501 in FIG. 19 merely reflects that the signal from the proximity sensor 35 can be processed by the processing unit 19 after the storing of the ejection event (step 501). This can suitably be done once immediately after beginning ejection (as, for example, determined by ejection sensor 33) or immediately after finishing ejection. The presence of a solid object during that one time may be sufficient to log the ejection event as an injection event.

If the distance to a solid object is larger than the set threshold value T the ejection event is tagged as a priming event in step 504. If the there is a solid object within the threshold distance the ejection event is determined to be an injection event and the ejection event is tagged as such in step 505.

Information about the ejection event can then be displayed, step 506, on the first display 3 of the device. Preferably this occurs when ejection is completed as detected by dose setting sensor 17 or by ejection sensor 33. The user may then be given the opportunity in 508, to tag the ejection event in step 507 in the same manner as the glucose measurement event can be tagged. Preferably, the ejection event is only displayed on the first display 3 after ejection is completed. Tagging is suitably available within a certain time frame which can be 10 seconds. After that time frame the device shuts down in step 509 in order to save battery.

Again tagging can include one of the following events: if the user recently has taken a meal, if the user recently has carried out exercise, or if the user is feeling ill. For example by scrolling in the menu, the user first selects "TAG" and then one of "MEAL", "EXERCISE" and "ILLNESS".

The injection event can be automatically connected in the database 200 to a blood glucose measurement event in the database if the injection is made within a certain time of making a blood glucose measurement. That time can be 60 minutes, 30 minutes, 20 minutes, 15 minutes or 10 minutes. Preferably the time is 30 minutes after or before a blood glucose measuring event. Even more preferably, the time is 30 minutes after a blood glucose measurement event. This is carried out by storing in the memory 38 information that links or associates the injection event to the blood glucose measurement event.

The ejection event in the database 200 can be stored together with information if whether the ejection was an injection event or a priming event. The electronic log can be such that ejection events that are tagged as priming events are not accessible to the user via the user interface on the device 1. For example, they are only accessible after entering a code or through the data port, or both. This has the advantage that the user does not usually have access to and does not see the priming events and does not confuse the injection events in the log with the priming events. The priming events of the database are still accessible for a medical doctor or nurse that wants to check up on the compliance of the user, or a technician that performs service on the device. The injection events in the log are, however, suitably accessible to the user. For example the user may view information about these on the first display.

FIG. 16 is a schematic representation of an example of a database 200 containing two exemplary entries representing insulin ejection events. Event 201 is an example of a priming event and event 202 is an example of an injection event, which has been tagged with MEAL by the user because the patient has taken a meal in connection with the injection. Event 201 is present in the database 200 but may not be visible to the user through the interface of the device 1.

The database 200 can be such that ejection events are classified as injection events by default and storing a tag with the ejection event classifies it as a priming event as seen in FIG. 16. Alternatively, the database 200 can be such that that ejection events are priming events by default and storing a tag with the ejection event classifies it as an injection event.

Figure 22:
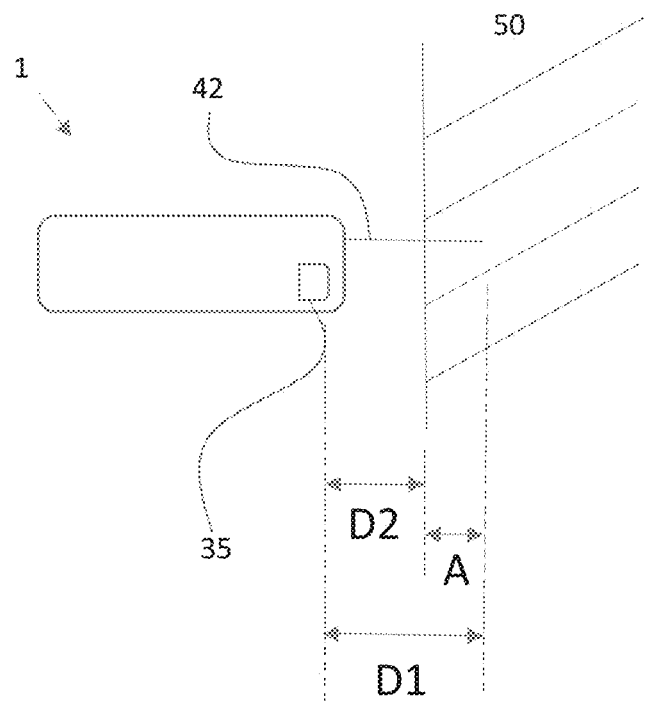

In an alternative embodiment the method the electronic log takes the length of the needle into account in a manner shown in FIG. 22. In this embodiment an ejection event is classified as an injection, if, when insulin is ejected, the distance from the sensor to the tip of the needle ($D_1$) is larger than the distance from the sensor to an object ($D_2$) and where $$D_1 - D_2 \geq \text{distance } A$$

In this embodiment, an ejection event is logged as an injection event if the needle has entered at least A mm into the solid object, i.e. the body of the patient. A shall be chosen to accommodate the fact that the needle shall enter the body sufficiently and that also take into account that injection can be done through clothing such as a loose-knitted sweater. A can for example be, 0.1 mm, 0.5 mm, 1 mm, 5 mm or 10 mm, depending on the length of the needle. Thus the length of the needle has to be entered into and stored in the memory of the processing unit 19 or as hardware.

The invention claimed is:

1. A portable medical device for injecting a medicament into a patient, comprising:
   a control circuit with a memory, the control circuit automatically storing in the memory an ejection event including an amount of the medicament that is ejected from the portable medical device during the ejection event; and
   a proximity sensor operatively coupled and communicating proximity data to the control circuit, and the proximity sensor configured to sense, at a time that the medicament is ejected, proximity of a solid object located within a predetermined threshold distance from a fixed location on the portable medical device in an ejection direction of the portable medical device without the proximity sensor making contact with the solid object; and wherein, based on the proximity data, the control circuit is configured to tag the ejection event as an injection event if the ejection takes place within the threshold distance of the solid object and to tag the ejection event as a priming ejection if the ejection does not take place within the threshold distance of the solid object.

2. The portable medical device of claim 1, wherein information about the injection event is accessible to the user on a user interface and information about the priming event is not accessible to the user via the user interface.

3. The portable medical device of claim 2, wherein the user interface is part of the portable medical device in the form of an electronic display.

4. The portable medical device of claim 1, further comprising a user interface and wherein the injection event is taggable via the user interface by a user with additional information selected from one or more of a blood glucose measurement, a health status, a meal or exercise.

5. The portable medical device of claim 1, wherein the control circuit is configured to automatically tag the injection event with a value from a blood glucose measurement if the blood glucose measurement is made within a predetermined amount of time from a time of the injection event.

6. The portable medical device of claim 1, wherein the proximity sensor comprises a thermal sensor.

7. The portable medical device of claim 1, wherein the proximity sensor comprises an infrared sensor.

8. The portable medical device of claim 1, wherein the proximity sensor comprises an ultrasound sensor.

9. The portable medical device of claim 1, wherein the proximity sensor comprises a radio frequency sensor.

10. The portable medical device of claim 1, wherein the solid object that leads to tagging the ejection event as an injection event includes bare skin and skin covered by clothing.

11. A portable medical device for injecting a medicament into a patient, comprising:
a control circuit with a memory, the control circuit automatically storing in the memory an ejection event including an amount of the medicament that is ejected from the portable medical device during the ejection event; and
a proximity sensor operatively coupled and communicating proximity data to the control circuit, and the proximity sensor configured to sense, at a time that the medicament is ejected, proximity of a solid object located within a predetermined threshold distance from a fixed location on the portable medical device in an ejection direction of the portable medical device without the proximity sensor making contact with the solid object; and
wherein, based on the proximity data, the control circuit is configured to tag the ejection event as an injection event if a distance (D1) from the proximity sensor to a tip of a needle through which the medicament is ejected is larger than a distance (D2) from the proximity sensor to the solid object, and wherein $D1-D2 \geq 0.1$ mm, else tag the ejection event as a priming ejection.

12. The portable medical device of claim 11, wherein the solid object that leads to tagging the ejection event as an injection event includes bare skin and skin covered by clothing.

* * * * *